US012778810B2

(12) United States Patent
Mcgregor et al.

(10) Patent No.: US 12,778,810 B2
(45) Date of Patent: Nov. 3, 2026

(54) NEGATIVE PRESSURE WOUND THERAPY AND PHOTOTHERAPY

(71) Applicant: KCI Manufacturing Unlimited Company, Westmeath (IE)

(72) Inventors: Andrew J. Mcgregor, St. Paul, MN (US); Audrey Anne Sherman, St. Paul, MN (US); Amy K. McNulty, Stillwater, MN (US); Zhaohui Yang, St. Paul, MN (US); James Thielen, St. Paul, MN (US); Brett Sitter, St. Paul, MN (US)

(73) Assignee: KCI Manufacturing Unlimited Company, Westmeath (IE)

( * ) Notice: Subject to any disclaimer, the term of this patent is extended or adjusted under 35 U.S.C. 154(b) by 184 days.

(21) Appl. No.: 18/703,536

(22) PCT Filed: Sep. 29, 2022

(86) PCT No.: PCT/IB2022/059297
§ 371 (c)(1),
(2) Date: Apr. 22, 2024

(87) PCT Pub. No.: WO2023/067416
PCT Pub. Date: Apr. 27, 2023

(65) Prior Publication Data

US 2025/0235356 A1 Jul. 24, 2025

Related U.S. Application Data

(60) Provisional application No. 63/270,949, filed on Oct. 22, 2021.

(51) Int. Cl.
*A61F 13/00* (2024.01)
*A61F 13/05* (2024.01)
(Continued)

(52) U.S. Cl.
CPC ............... *A61F 13/05* (2024.01); *A61M 1/91* (2021.05); *A61N 5/062* (2013.01);
(Continued)

(58) Field of Classification Search
None
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | | |
|---|---|---|---|
| AU | 550575 | B2 | 3/1986 |
| AU | 745271 | B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Kim M Lewis

(57) ABSTRACT

A method for providing negative pressure wound therapy (NPWT) and phototherapy to a wound includes providing NPWT by drawing a negative pressure at the wound using a pump. The method also includes providing phototherapy by operating a light source to provide light having a specific wavelength to the wound. Drawing the negative pressure at the wound for NPWT changes a surface topology of the wound to expose different surfaces of the wound to the light for phototherapy.

18 Claims, 23 Drawing Sheets

(51) Int. Cl.
*A61M 1/00* (2006.01)
*A61N 5/06* (2006.01)

(52) U.S. Cl.
CPC ............... *A61F 2013/00604* (2013.01); *A61F 2013/00859* (2013.01); *A61M 2205/051* (2013.01); *A61M 2210/04* (2013.01); *A61N 2005/0662* (2013.01); *A61N 2005/0666* (2013.01); *A61N 2005/0667* (2013.01)

(56) References Cited

U.S. PATENT DOCUMENTS 2,632,443 A 3/1953 Lesher
2,682,873 A 7/1954 Evans et al.
2,910,763 A 11/1959 Lauterbach
2,969,057 A 1/1961 Simmons
3,066,672 A 12/1962 Crosby, Jr. et al.
3,367,332 A 2/1968 Groves
3,520,300 A 7/1970 Flower, Jr.
3,568,675 A 3/1971 Harvey
3,648,692 A 3/1972 Wheeler
3,682,180 A 8/1972 McFarlane
3,826,254 A 7/1974 Mellor
4,080,970 A 3/1978 Miller
4,096,853 A 6/1978 Weigand
4,139,004 A 2/1979 Gonzalez, Jr.
4,165,748 A 8/1979 Johnson
4,184,510 A 1/1980 Murry et al.
4,233,969 A 11/1980 Lock et al.
4,245,630 A 1/1981 Lloyd et al.
4,256,109 A 3/1981 Nichols
4,261,363 A 4/1981 Russo
4,275,721 A 6/1981 Olson
4,284,079 A 8/1981 Adair
4,297,995 A 11/1981 Golub
4,333,468 A 6/1982 Geist
4,373,519 A 2/1983 Errede et al.
4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Austad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,096,066 A * 8/2000 Chen ...................... A61N 5/062 607/91
6,135,116 A 10/2000 Vogel et al.
6,241,747 B1 6/2001 Ruff
6,287,316 B1 9/2001 Agarwal et al.
6,290,713 B1 * 9/2001 Russell ................ A61N 5/0616 607/91
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
6,994,702 B1 * 2/2006 Johnson .................. A61F 13/05 606/14
7,304,201 B2 * 12/2007 Holloway ............... A61F 15/00 602/41
7,846,141 B2 12/2010 Weston
8,062,273 B2 11/2011 Weston
8,216,198 B2 7/2012 Heagle et al.
8,251,979 B2 8/2012 Malhi
8,257,327 B2 9/2012 Blott et al.
8,398,614 B2 3/2013 Blott et al.
8,449,509 B2 5/2013 Weston
8,529,548 B2 9/2013 Blott et al.
8,535,296 B2 9/2013 Blott et al.
8,551,060 B2 10/2013 Schuessler et al.
8,568,386 B2 10/2013 Malhi
8,679,081 B2 3/2014 Heagle et al.
8,834,451 B2 9/2014 Blott et al.
8,926,592 B2 1/2015 Blott et al.
9,017,302 B2 4/2015 Vitaris et al.
9,198,801 B2 12/2015 Weston
9,211,365 B2 12/2015 Weston
9,289,542 B2 3/2016 Blott et al.
9,918,733 B2 * 3/2018 Ingram .................. A61B 17/32
10,918,770 B2 * 2/2021 Fewkes ................... A61M 1/80
2002/0077661 A1 6/2002 Saadat
2002/0115951 A1 8/2002 Norstrem et al.
2002/0120185 A1 8/2002 Johnson
2002/0143286 A1 10/2002 Tumey
2014/0163491 A1 6/2014 Schuessler et al.
2014/0343478 A1 11/2014 Brennan et al.
2015/0080788 A1 3/2015 Blott et al.
2019/0070432 A1 3/2019 Hill et al.
2020/0046569 A1 * 2/2020 Quisenberry ........... A61F 13/05
2020/0085625 A1 3/2020 Bellini et al.

FOREIGN PATENT DOCUMENTS

AU 755496 B2 12/2002
CA 2005436 A1 6/1990
DE 2640413 A1 3/1978

(56) References Cited

FOREIGN PATENT DOCUMENTS

| | | | |
|---|---|---|---|
| DE | 4306478 | A1 | 9/1994 |
| DE | 29504378 | U1 | 9/1995 |
| EP | 0100148 | A1 | 2/1984 |
| EP | 117632 | A2 | 9/1984 |
| EP | 161865 | A2 | 11/1985 |
| EP | 358302 | A2 | 3/1990 |
| EP | 1018967 | A1 | 7/2000 |
| EP | 3413972 | B1 | 9/2020 |
| GB | 692578 | A | 6/1953 |
| GB | 2195255 | A | 4/1988 |
| GB | 2197789 | A | 6/1988 |
| GB | 2220357 | A | 1/1990 |
| GB | 2235877 | A | 3/1991 |
| GB | 2329127 | A | 3/1999 |
| GB | 2333965 | A | 8/1999 |
| JP | 4129536 | B2 | 8/2008 |
| SG | 71559 | | 4/2002 |
| WO | 80/02182 | A1 | 10/1980 |
| WO | 8704626 | A1 | 8/1987 |
| WO | 90010424 | A1 | 9/1990 |
| WO | 93009727 | A1 | 5/1993 |
| WO | 94020041 | A1 | 9/1994 |
| WO | 9605873 | A1 | 2/1996 |
| WO | 9718007 | A1 | 5/1997 |
| WO | 9913793 | A1 | 3/1999 |
| WO | 2021156711 | A1 | 8/2021 |

OTHER PUBLICATIONS

Susan Mendez-Eatmen, RN; “When wounds Won’t Heal” RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; “Reliable, Inexpensive and Simple Suction Dressings”; Letter to the Editor, British Journal of Plastic Surgery, 1998, vol. 51 (3), p. 267; Elsevier Science/The British Association of Plastic Surgeons, UK.

S.E. Greer, et al. “The Use of Subatmospheric Pressure Dressing Therapy to Close Lymphocutaneous Fistulas of the Groin” British Journal of Plastic Surgery (2000), 53, pp. 484-487.

George V. Letsou, MD., et al; “Stimulation of Adenylate Cyclase Activity in Cultured Endothelial Cells Subjected to Cyclic Stretch”; Journal of Cardiovascular Surgery, 31, 1990, pp. 634-639.

Orringer, Jay, et al; “Management of Wounds in Patients with Complex Enterocutaneous Fistulas”; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713, Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; “Medical Textiles: Application of an Absorbable Barbed Bi-directional Surgical Suture”; Journal of Textile and Apparel, Technology and Management, vol. 2, Issue 2, Spring 2002, pp. 1-5.

Kostyuchenok, B.M., et al; “Vacuum Treatment in the Surgical Management of Purulent Wounds”; Vestnik Khirurgi, Sep. 1986, pp. 18-21 and 6 page English translation thereof.

Davydov, Yu. A., et al; “Vacuum Therapy in the Treatment of Purulent Lactation Mastitis”; Vestnik Khirurgi, May 14, 1986, pp. 66-70, and 9 page English translation thereof.

Yusupov. Yu.N., et al; “Active Wound Drainage”, Vestnki Khirurgi, vol. 138, Issue 4, 1987, and 7 page English translation thereof.

Davydov, Yu.A., et al; “Bacteriological and Cytological Assessment of Vacuum Therapy for Purulent Wounds”; Vestnik Khirugi, Oct. 1988, pp. 48-52, and 8 page English translation thereof.

Davydov, Yu.A., et al; “Concepts for the Clinical-Biological Management of the Wound Process in the Treatment of Purulent Wounds by Means of Vacuum Therapy”; Vestnik Khirurgi, Jul. 7, 1980, pp. 132-136, and 8 page English translation thereof.

Chariker, Mark E., M.D., et al; “Effective Management of incisional and cutaneous fistulae with closed suction wound drainage”; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: “Irrigation Treatment of Leg Ulcers”, The Lancet, Sep. 3, 1983, pp. 532-534.

Chinn, Steven D. et al.: “Closed Wound Suction Drainage”, The Journal of Foot Surgery, vol. 24, No. 1, 1985, pp. 76-81.

Arnljots, Björn et al.: “Irrigation Treatment in Split-Thickness Skin Grafting of Intractable Leg Ulcers”, Scand J. Plast Reconstr. Surg., No. 19, 1985, pp. 211-213.

Svedman, P.: “A Dressing Allowing Continuous Treatment of a Biosurface”, IRCS Medical Science: Biomedical Technology, Clinical Medicine, Surgery and Transplantation, vol. 7, 1979, p. 221.

Svedman, P. et al: “A Dressing System Providing Fluid Supply and Suction Drainage Used for Continuous of Intermittent Irrigation”, Annals of Plastic Surgery, vol. 17, No. 2, Aug. 1986, pp. 125-133.

N.A. Bagautdinov, “Variant of External Vacuum Aspiration in the Treatment of Purulent Diseases of Soft Tissues,” Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, “Managing Draining Wounds and Fistulae: New and Established Methods,” Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, “Vacuum Therapy in the Treatment of Peripheral Blood Vessels,” Timok Medical Journal 11 (1986), pp. 161-164 (certified translation).

F.E. Johnson, “An Improved Technique for Skin Graft Placement Using a Suction Drain,” Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, “The ‘Sandwich Technique’ in the Management of the Open Abdomen,” British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, “Vacuum-Assisted Closure: A New Method for Wound Control and Treatment: Animal Studies and Basic Foundation,” Annals of Plastic Surgery 38 (1997), pp. 553-562 (Morykwas I).

C.E. Tennants, “The Use of Hypermia in the Postoperative Treatment of Lesions of the Extremities and Thorax,” Journal of the American Medical Association 64 (1915), pp. 1548-1549.

Selections from W. Meyer and V. Schmieden, Bier’s Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) (“Solovev Guidelines”).

V.A. Kuznetsov & N.a. Bagautdinov, “Vacuum and Vacuum-Sorption Treatment of Open Septic Wounds,” in II All-Union Conference on Wounds and Wound Infections: Presentation Abstracts,

(56) References Cited

OTHER PUBLICATIONS edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion for Corresponding Application No. PCT/IB2022/059297, mailed Dec. 7, 2022.

* cited by examiner

NEGATIVE PRESSURE WOUND THERAPY AND PHOTOTHERAPY

CROSS-REFERENCE TO RELATED APPLICATIONS

This application is a U.S. National Stage Entry of PCT/IB2022/059297, filed Sep. 29, 2022, which claims the benefit, under 35 U.S.C. § 119(e), of U.S. Provisional Application No. 63/270,949, filed on Oct. 22, 2021, which is incorporated herein by reference in its entirety.

BACKGROUND

The present disclosure relates generally to a wound therapy system, and more particularly to a negative pressure wound therapy system.

SUMMARY

One implementation of the present disclosure is a wound dressing for use with a negative pressure wound therapy (NPWT) device, according to some embodiments. In some embodiments, the wound dressing includes a manifold layer, a lightguide, and a drape layer. In some embodiments, the manifold layer extends over a wound for NPWT. In some embodiments, the lightguide is positioned below the manifold layer and above the wound. In some embodiments, the lightguide is configured to receive light at a first portion, transfer the light through the lightguide, and emit the light towards the wound at a second portion for phototherapy of the wound. In some embodiments, the drape layer covers the manifold layer and the lightguide. In some embodiments, the drape layer sealingly couples with skin surrounding the wound and defines a sealed inner volume of the wound dressing. In some embodiments, the drape layer includes a first opening for drawing a negative pressure at the sealed inner volume of the wound dressing, and a second opening for providing light to the first portion of the lightguide for phototherapy of the wound.

In some embodiments, the lightguide includes multiple openings extending through the lightguide. In some embodiments, the openings are configured to define a path for fluid to transfer from the wound to the manifold layer through the lightguide when the negative pressure is drawn at the wound.

In some embodiments, the openings are arranged in an array. In some embodiments, at least one of a size or a shape of the openings varies along at least one dimension of the array. In some embodiments, the size and shape of the openings is uniform along at least one dimension of the array.

In some embodiments, the wound dressing is configured for use with a coupler assembly. In some embodiments, the coupler assembly includes a coupler configured to couple with the first opening and the second opening of the drape layer for drawing the negative pressure at the wound and for providing light to the lightguide for phototherapy.

In some embodiments, the coupler assembly includes a first tubular member and a second tubular member. In some embodiments, the first tubular member is configured to fluidly couple with the first opening of the wound dressing through the coupler for drawing the negative pressure at the wound and the second tubular member is operably coupled with the second opening for delivering light to the wound for phototherapy.

In some embodiments, the coupler assembly includes a light source positioned within the coupler configured to emit light through the second opening to the lightguide. In some embodiments, the second tubular member is a wire configured to provide electrical energy to the light source.

In some embodiments, the second tubular member is a fiber optic cable configured to receive light from an external light source and provide the light through the second tubular member to the lightguide through the second opening. In some embodiments, the coupler assembly further includes a third tubular member configured to fluidly couple with a third opening of the drape layer. In some embodiments, the third tubular member is configured to provide an instillation fluid to the interior of the wound dressing through the third opening of the drape.

In some embodiments, the instillation fluid includes a photosensitizing agent. In some embodiments, the photosensitizing agent is configured to increase an absorption of the light into tissue of the wound.

In some embodiments, the photosensitizing agent is Methylene blue or O-toluidine blue. In some embodiments, an interior surface of the drape layer includes a reflective material. In some embodiments, the reflective material is configured to reflect light towards the wound to improve an efficacy of the phototherapy.

Another implementation of the present disclosure is a negative pressure wound therapy (NPWT) and phototherapy system, according to some embodiments. In some embodiments, the system includes a wound dressing configured to cover a wound, a therapy device, and a light source. In some embodiments, the therapy device is configured to draw a negative pressure at the wound for NPWT. In some embodiments, the light source is configured to provide light to the wound within the wound dressing for photo therapy. In some embodiments, the system is configured to provide both NPWT and phototherapy to the wound consecutively or at least partially concurrently. In some embodiments, providing NPWT changes a surface topology of the wound prior to or at least partially concurrently with providing phototherapy.

In some embodiments, changing the surface topology of the wound improves an efficacy of the phototherapy by exposing additional surfaces of the wound to the light provided for phototherapy.

In some embodiments, the wound dressing includes a manifold layer extending over the wound for NPWT, a lightguide, and a drape layer. In some embodiments, the lightguide is positioned below the manifold layer and above the wound. In some embodiments, the lightguide is configured to receive light at a first portion, transfer the light through the lightguide, and emit the light towards the wound at a second portion for the phototherapy of the wound. In some embodiments, the drape layer covers the manifold layer and the lightguide. In some embodiments, the drape layer sealingly couples with skin surrounding the wound and defines a sealed inner volume of the wound dressing. In some embodiments, the drape layer includes a first opening for drawing a negative pressure at the sealed inner volume of the wound dressing, and a second opening for providing light to the first portion of the lightguide for the phototherapy of the wound.

In some embodiments, the system further includes a coupler assembly. In some embodiments, the coupler assembly includes a coupler configured to couple with a first opening and a second opening of the wound dressing for drawing the negative pressure at the wound and for providing light to the wound for the phototherapy.

In some embodiments, the coupler assembly includes a first tubular member and a second tubular member. In some embodiments, the first tubular member is configured to fluidly couple with the first opening of the wound dressing through the coupler for drawing the negative pressure at the wound and the second tubular member is operably coupled with the second opening for delivering light to the wound for phototherapy.

In some embodiments, the coupler assembly includes a light source positioned within the coupler configured to emit light through the second opening to the wound. In some embodiments, the second tubular member is a wire configured to provide electrical energy to the light source.

In some embodiments, the second tubular member is a fiber optic cable configured to receive light from an external light source and provide the light through the second tubular member to the lightguide through the second opening. In some embodiments, the coupler assembly further includes a third tubular member configured to fluidly couple with a third opening of the drape. In some embodiments, the therapy device is configured to provide an instillation fluid to the interior of the wound dressing through the third opening of the drape.

In some embodiments, the instillation fluid includes a photosensitizing agent. In some embodiments, the photosensitizing agent is configured to increase an absorption of the light into tissue of the wound. In some embodiments, the photosensitizing agent is Methylene blue or O-toluidine blue.

In some embodiments, the light source is positioned within the wound dressing. In some embodiments, the light source is positioned on a wound facing surface of a manifold layer of the wound dressing. In some embodiments, the light source is positioned on a wound facing surface of a drape layer of the wound dressing.

In some embodiments, the light source is positioned external to the wound dressing. In some embodiments, the light source is positioned within the therapy device. In some embodiments, the light provided by the light source is at least one of visible light, UV light, blue light, infrared light, near infrared light, or red light. In some embodiments, the light provided by the light source for the phototherapy has a wavelength of 207 nanometers.

In some embodiments, the light provided by the light source is visible light, and microfilm layers are positioned between the light source and the wound. In some embodiments, the microfilm layers are configured to filter the light so that light having a different wavelength is provided to the wound for the phototherapy.

In some embodiments, the light source is configured to output light having a single wavelength. In some embodiments, the light source is configured to output light at different wavelengths. In some embodiments, the light source is configured to operate to provide light having a first wavelength over a first time period and light having a second wavelength over a second time period to provide different types of phototherapy.

In some embodiments, the therapy device is configured to draw a static negative pressure at the wound. In some embodiments, the therapy device is configured to draw a dynamic negative pressure at the wound. In some embodiments, drawing the dynamic negative pressure includes oscillating the negative pressure at the wound over time. In some embodiments, oscillating the negative pressure changes the surface topology of the wound over time to expose different surfaces of the wound for phototherapy.

Another implementation of the present disclosure is a method for providing negative pressure wound therapy (NPWT) and phototherapy to a wound, according to some embodiments. In some embodiments, the method includes providing NPWT by drawing a negative pressure at the wound using a pump. In some embodiments, the method includes providing phototherapy by operating a light source to provide light having a specific wavelength to the wound. In some embodiments, drawing the negative pressure at the wound for NPWT changes a surface topology of the wound to expose different surfaces of the wound to the light for phototherapy.

In some embodiments, providing a photosensitizing agent to the wound prior to or at least partially concurrently with operating the light source to provide the light for phototherapy.

In some embodiments, the photosensitizing agent is Methylene blue or O-toluidine blue. In some embodiments, the photosensitizing agent is suspended in a fluid and providing the photosensitizing agent includes pumping the fluid to the wound.

In some embodiments, providing the NPWT and providing the phototherapy is performed at least partially simultaneously. In some embodiments, drawing the negative pressure and the wound using the pump includes oscillating a negative pressure at the wound over time using the pump. In some embodiments, the phototherapy is provided while oscillating the negative pressure at the wound over time. In some embodiments, the specific wavelength is 207 nanometers and the light is UVC light.

In some embodiments, the method further includes filling an interior of a dressing positioned over the wound with instillation fluid. In some embodiments, the light for phototherapy is directed through fluid in a tubular member that supplies the instillation fluid, and through the instillation fluid in the interior to the wound.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
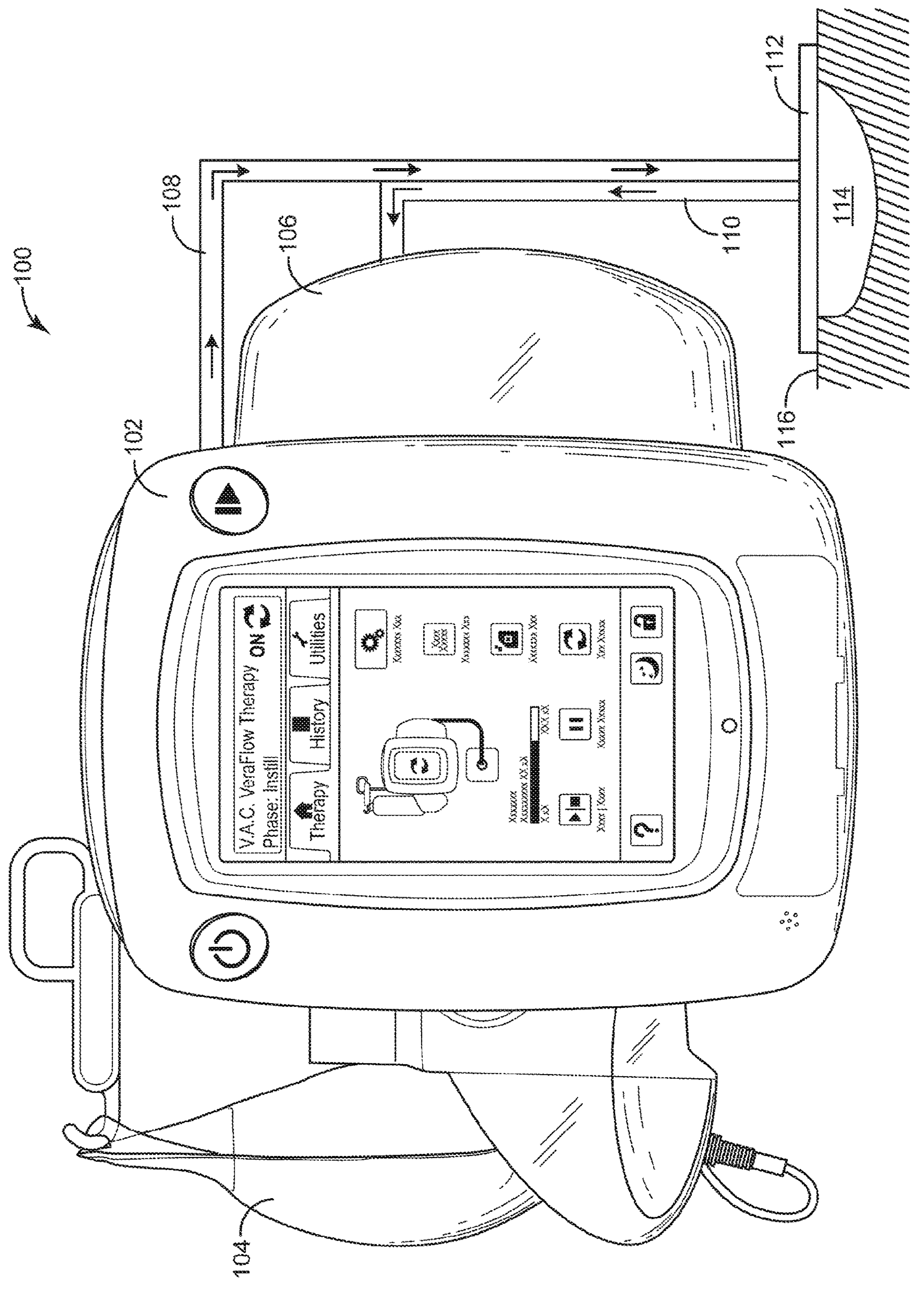
FIG. 1 is a block diagram of a wound therapy system including a therapy device coupled to a wound dressing via tubing, according to some embodiments.

Referring generally to the FIGURES, systems and methods for providing NPWT and phototherapy are shown, according to various embodiments. NPWT can be provided to both facilitate healing progression of the wound, remove wound exudate, etc., and also to adjust, actuate, change, etc., a surface topology of the wound bed. The phototherapy may include providing UV light, blue light, red light, etc., to the wound bed to facilitate healing or disinfection of the wound. When combined with NPWT, the efficacy of the phototherapy can be improved since varying the surface topology of the wound bed with NPWT (e.g., dynamic or oscillating NPWT) may expose additional surfaces of the wound for phototherapy, thereby improving the disinfection characteristics of phototherapy and facilitating healing progression of the wound. Advantageously, providing phototherapy may also disinfect and function as an anti-microbial for the wound.

Wound Therapy System

Referring now to FIGS. 1-4, a NPWT system 100 is shown, according to an exemplary embodiment. NPWT system 100 is shown to include a therapy device 102 fluidly connected to a wound dressing 112 via tubing 108 and 110. Wound dressing 112 may be adhered or sealed to a patient's skin 116 surrounding a wound 114. Several examples of wound dressings 112 which can be used in combination with NPWT system 100 are described in detail in U.S. Pat. No. 7,651,484 granted Jan. 26, 2010, U.S. Pat. No. 8,394,081 granted Mar. 12, 2013, and U.S. Pat. No. 10,232,155 granted Mar. 19, 2019. The entire disclosure of each of these patents is incorporated by reference herein.

Therapy device 102 can be configured to provide negative pressure wound therapy by reducing the pressure at wound 114. Therapy device 102 can draw a vacuum at wound 114 (relative to atmospheric pressure) by removing wound exudate, air, and other fluids from wound 114. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound 114 may include instillation fluid 105 previously delivered to wound 114. Instillation fluid 105 can include, for example, a cleansing fluid, a prescribed fluid, a medicated fluid, an antibiotic fluid, or any other type of fluid which can be delivered to wound 114 during wound treatment. Instillation fluid 105 may be held in an instillation fluid canister 104 and controllably dispensed to wound 114 via instillation fluid tubing 108. In some embodiments, instillation fluid canister 104 is detachable from therapy device 102 to allow canister 106 to be refilled and replaced as needed.

The fluids 107 removed from wound 114 pass through removed fluid tubing 110 and are collected in removed fluid canister 106. Removed fluid canister 106 may be a component of therapy device 102 configured to collect wound exudate and other fluids 107 removed from wound 114. In some embodiments, removed fluid canister 106 is detachable from therapy device 102 to allow canister 106 to be emptied and replaced as needed. A lower portion of canister 106 may be filled with wound exudate and other fluids 107 removed from wound 114, whereas an upper portion of canister 106 may be filled with air. Therapy device 102 can be configured to draw a vacuum within canister 106 by pumping air out of canister 106. The reduced pressure within canister 106 can be translated to wound dressing 112 and wound 114 via tubing 110 such that wound dressing 112 and wound 114 are maintained at the same pressure as canister 106.

Figure 2:
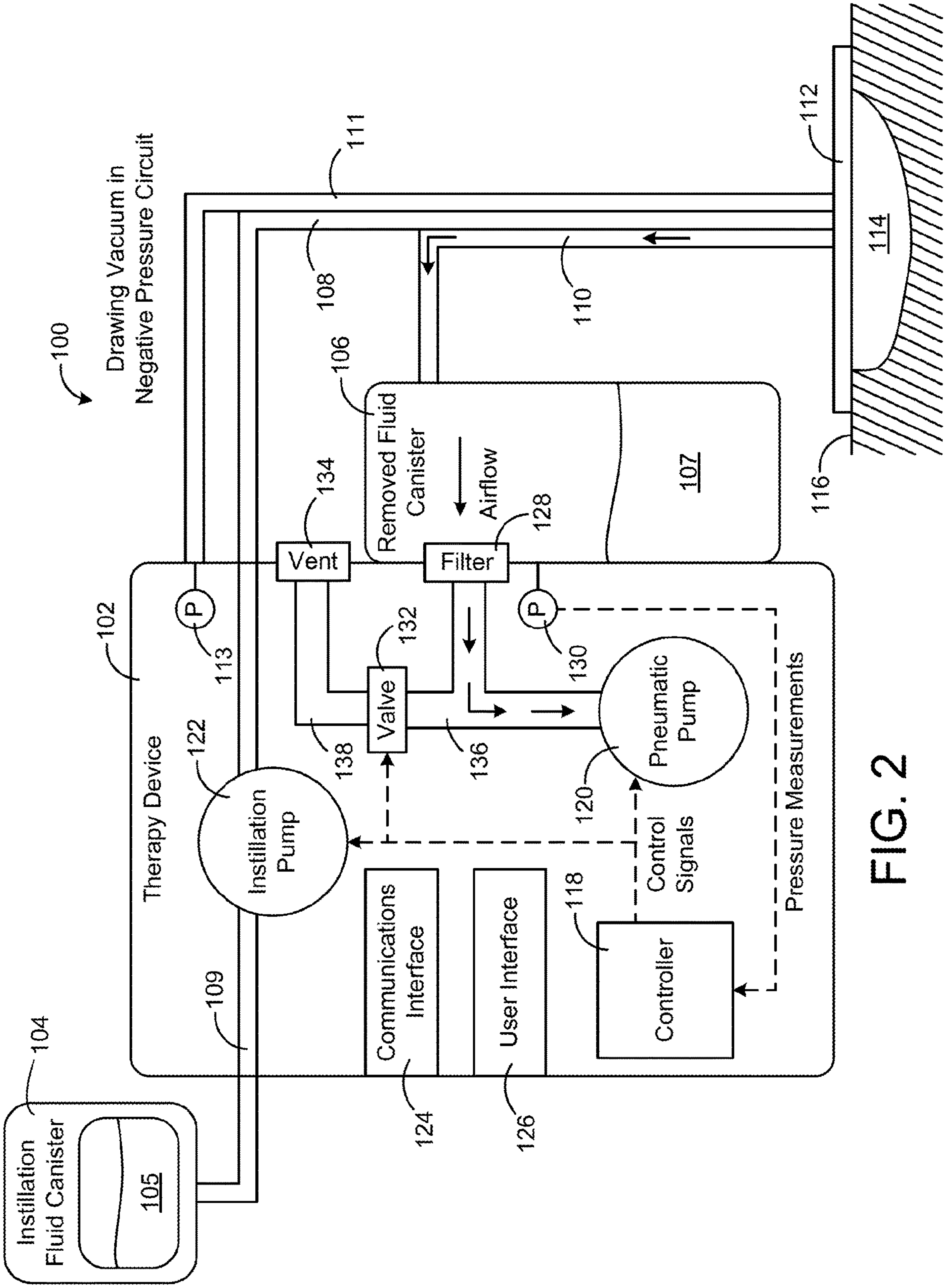
FIG. 2 is a block diagram illustrating the therapy device of FIG. 1 in greater detail when the therapy device operates to draw a vacuum within a negative pressure circuit, according to some embodiments.
Figure 3A:
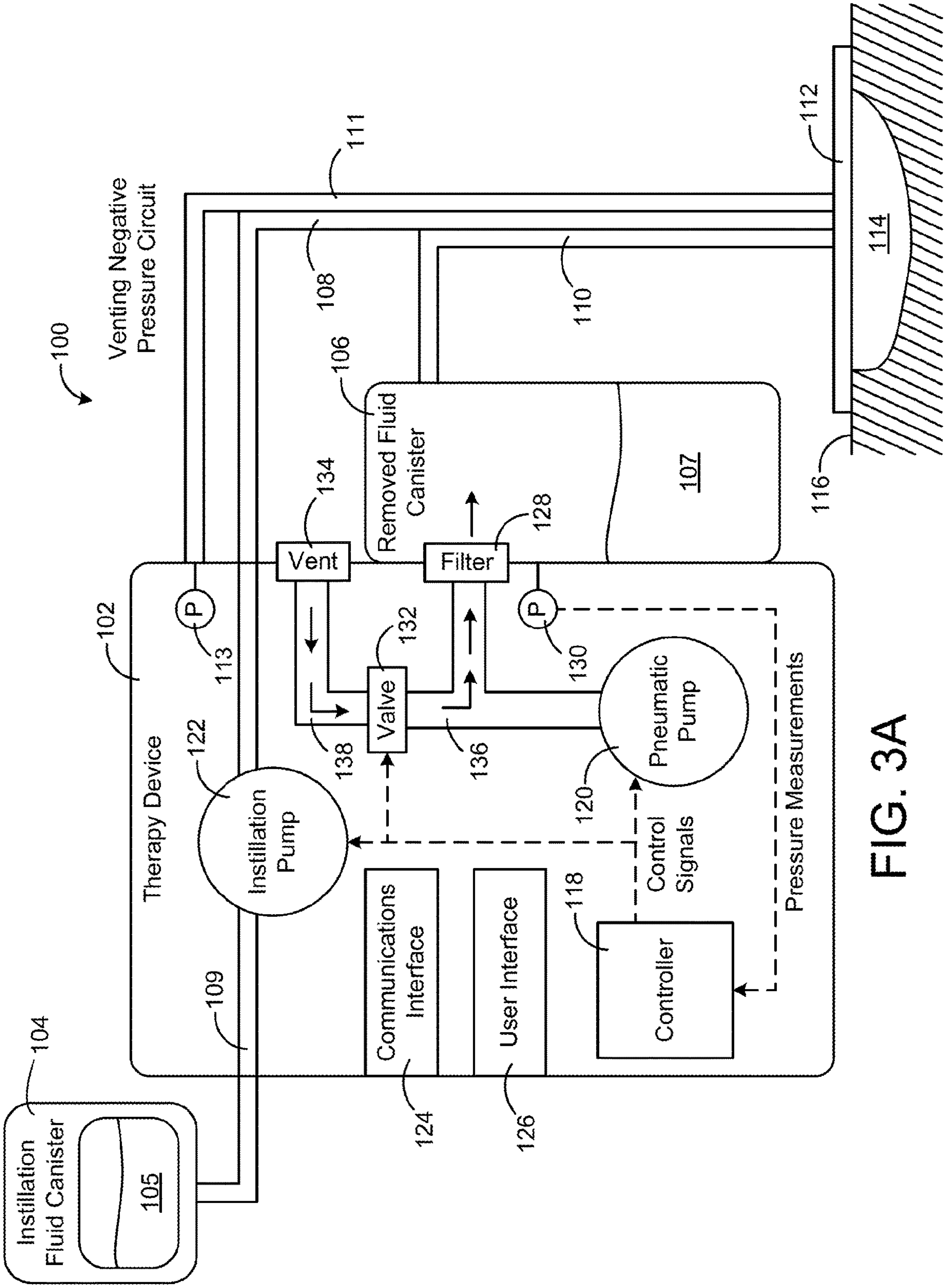
FIG. 3A is a block diagram illustrating the therapy device of FIG. 1 in greater detail when the therapy device operates to vent the negative pressure circuit, according to some embodiments.
Figure 3B:
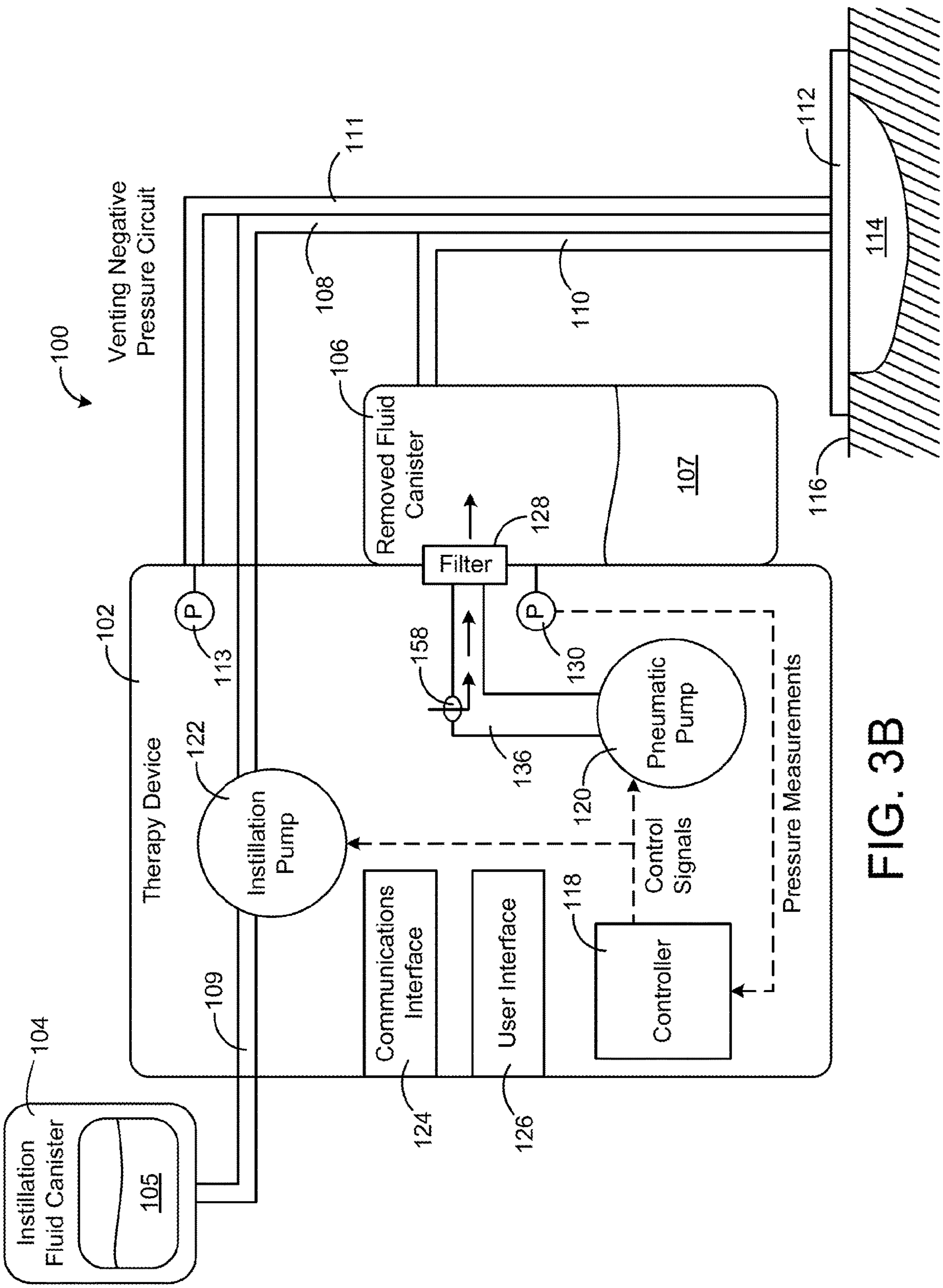
FIG. 3B is a block diagram illustrating the therapy device of FIG. 1 in greater detail when the therapy device uses an orifice to vent the negative pressure circuit, according to some embodiments.
Figure 4:
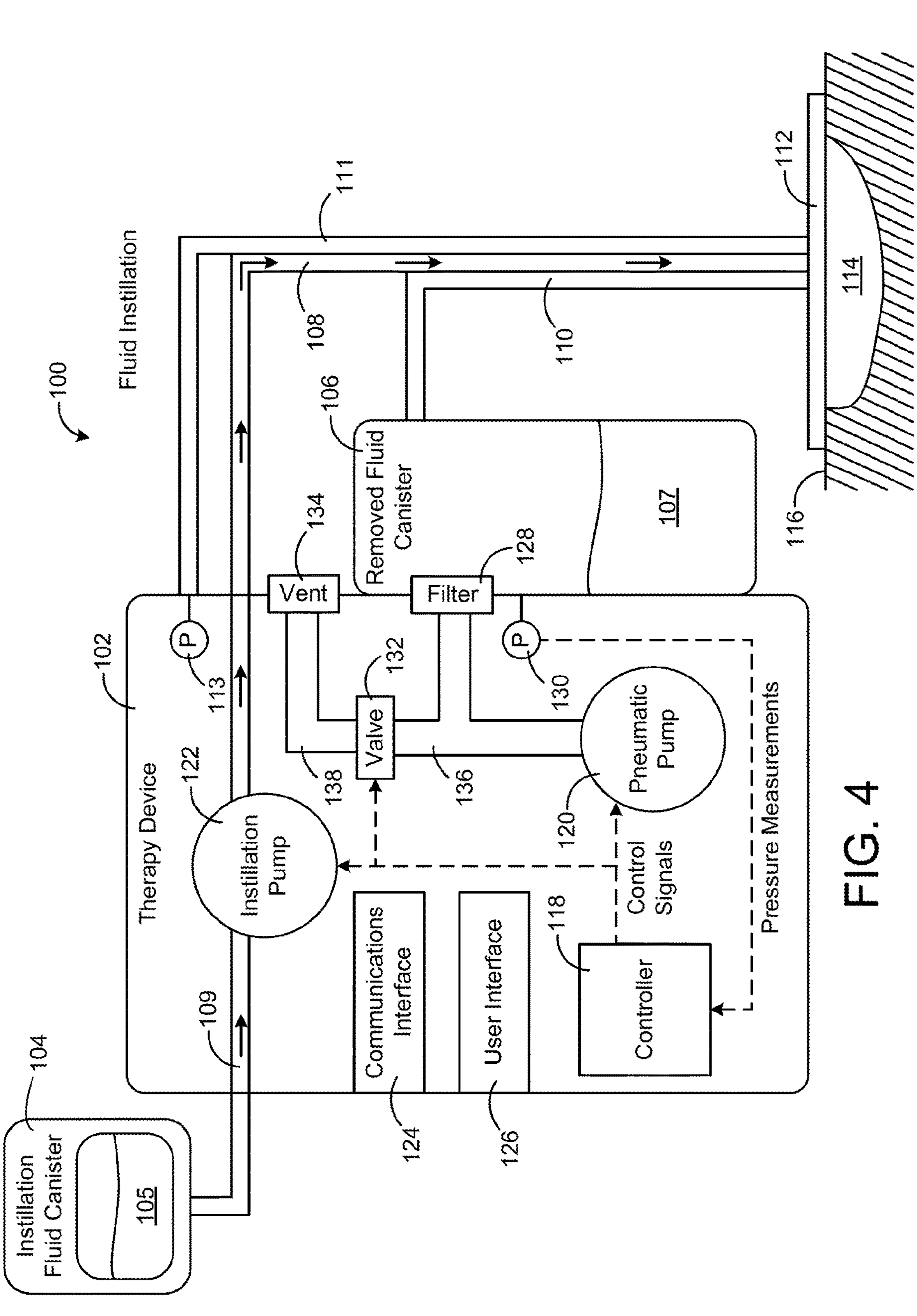
FIG. 4 is a block diagram illustrating the therapy device of FIG. 1 in greater detail when the therapy device operates to deliver instillation fluid to the wound dressing and/or a wound, according to some embodiments.

Referring particularly to FIGS. 2-4, block diagrams illustrating therapy device 102 in greater detail are shown, according to an exemplary embodiment. Therapy device 102 is shown to include a pneumatic pump 120, an instillation pump 122, a valve 132, a filter 128, and a controller 118. Pneumatic pump 120 can be fluidly coupled to removed fluid canister 106 (e.g., via conduit 136) and can be configured to draw a vacuum within canister 106 by pumping air out of canister 106. In some embodiments, pneumatic pump 120 is configured to operate in both a forward direction and a reverse direction. For example, pneumatic pump 120 can operate in the forward direction to pump air out of canister 106 and decrease the pressure within canister 106. Pneumatic pump 120 can operate in the reverse direction to pump air into canister 106 and increase the pressure within canister 106. Pneumatic pump 120 can be controlled by controller 118, described in greater detail below.

Similarly, instillation pump 122 can be fluidly coupled to instillation fluid canister 104 via tubing 109 and fluidly coupled to wound dressing 112 via tubing 108. Instillation pump 122 can be operated to deliver instillation fluid 105 to wound dressing 112 and wound 114 by pumping instillation fluid 105 through tubing 109 and tubing 108, as shown in FIG. 4. Instillation pump 122 can be controlled by controller 118, described in greater detail below.

Filter 128 can be positioned between removed fluid canister 106 and pneumatic pump 120 (e.g., along conduit 136) such that the air pumped out of canister 106 passes through filter 128. Filter 128 can be configured to prevent liquid or solid particles from entering conduit 136 and reaching pneumatic pump 120. Filter 128 may include, for example, a bacterial filter that is hydrophobic and/or lipophilic such that aqueous and/or oily liquids will bead on the surface of filter 128. Pneumatic pump 120 can be configured to provide sufficient airflow through filter 128 that the pressure drop across filter 128 is not substantial (e.g., such that the pressure drop will not substantially interfere with the application of negative pressure to wound 114 from therapy device 102).

In some embodiments, therapy device 102 operates a valve 132 to controllably vent the negative pressure circuit, as shown in FIG. 3A. Valve 132 can be fluidly connected with pneumatic pump 120 and filter 128 via conduit 136. In some embodiments, valve 132 is configured to control airflow between conduit 136 and the environment around therapy device 102. For example, valve 132 can be opened to allow airflow into conduit 136 via vent 134 and conduit 138, and closed to prevent airflow into conduit 136 via vent 134 and conduit 138. Valve 132 can be opened and closed by controller 118, described in greater detail below. When valve 132 is closed, pneumatic pump 120 can draw a vacuum within a negative pressure circuit by causing airflow through filter 128 in a first direction, as shown in FIG. 2. The negative pressure circuit may include any component of system 100 that can be maintained at a negative pressure when performing negative pressure wound therapy (e.g., conduit 136, removed fluid canister 106, tubing 110, wound dressing 112, and/or wound 114). For example, the negative pressure circuit may include conduit 136, removed fluid canister 106, tubing 110, wound dressing 112, and/or wound 114. When valve 132 is open, airflow from the environment around therapy device 102 may enter conduit 136 via vent 134 and conduit 138 and fill the vacuum within the negative pressure circuit. The airflow from conduit 136 into canister 106 and other volumes within the negative pressure circuit may pass through filter 128 in a second direction, opposite the first direction, as shown in FIG. 3A.

In some embodiments, therapy device 102 vents the negative pressure circuit via an orifice 158, as shown in FIG. 3B. Orifice 158 may be a small opening in conduit 136 or any other component of the negative pressure circuit (e.g., removed fluid canister 106, tubing 110, tubing 111, wound dressing 112, etc.) and may allow air to leak into the negative pressure circuit at a known rate. In some embodiments, therapy device 102 vents the negative pressure circuit via orifice 158 rather than operating valve 132. Valve 132 can be omitted from therapy device 102 for any embodiment in which orifice 158 is included. The rate at which air leaks into the negative pressure circuit via orifice 158 may be substantially constant or may vary as a function of the negative pressure, depending on the geometry of orifice 158. For embodiments in which the leak rate via orifice 158 is variable, controller 118 can use a stored relationship between negative pressure and leak rate to calculate the leak rate via orifice 158 based measurements of the negative pressure. Regardless of whether the leak rate via orifice 158 is substantially constant or variable, the leakage of air into the negative pressure circuit via orifice 158 can be used to generate a pressure decay curve for use in estimating volume 160 (see FIG. 8) of wound 114.

In some embodiments, therapy device 102 includes a variety of sensors. For example, therapy device 102 is shown to include a pressure sensor 130 configured to measure the pressure within canister 106 and/or the pressure at wound dressing 112 or wound 114. In some embodiments, therapy device 102 includes a pressure sensor 113 configured to measure the pressure within tubing 111. Tubing 111 may be connected to wound dressing 112 and may be dedicated to measuring the pressure at wound dressing 112 or wound 114 without having a secondary function such as channeling installation fluid 105 or wound exudate. In various embodiments, tubing 108, 110, and 111 may be physically separate tubes or separate lumens within a single tube that connects therapy device 102 to wound dressing 112. Accordingly, tubing 110 may be described as a negative pressure lumen that functions apply negative pressure wound dressing 112 or wound 114, whereas tubing 111 may be described as a sensing lumen configured to sense the pressure at wound dressing 112 or wound 114. Pressure sensors 130 and 113 can be located within therapy device 102, positioned at any location along tubing 108, 110, and 111, or located at wound dressing 112 in various embodiments. Pressure measurements recorded by pressure sensors 130 and/or 113 can be communicated to controller 118. Controller 118 use the pressure measurements as inputs to various pressure testing operations and control operations performed by controller 118.

Controller 118 can be configured to operate pneumatic pump 120, instillation pump 122, valve 132, and/or other controllable components of therapy device 102. In some embodiments, controller 118 performs a pressure testing procedure by applying a pressure stimulus to the negative pressure circuit. For example, controller 118 may instruct valve 132 to close and operate pneumatic pump 120 to establish negative pressure within the negative pressure circuit. Once the negative pressure has been established, controller 118 may deactivate pneumatic pump 120. Controller 118 may cause valve 132 to open for a predetermined amount of time and then close after the predetermined amount of time has elapsed.

In some embodiments, therapy device 102 includes a user interface 126. User interface 126 may include one or more buttons, dials, sliders, keys, or other input devices configured to receive input from a user. User interface 126 may also include one or more display devices (e.g., LEDs, LCD displays, etc.), speakers, tactile feedback devices, or other output devices configured to provide information to a user. In some embodiments, the pressure measurements recorded by pressure sensors 130 and/or 113 are presented to a user via user interface 126. User interface 126 can also display alerts generated by controller 118. For example, controller 118 can generate a "no canister" alert if canister 106 is not detected.

In some embodiments, therapy device 102 includes a data communications interface 124 (e.g., a USB port, a wireless transceiver, etc.) configured to receive and transmit data. Communications interface 124 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 124 can include a USB port or an Ethernet card and port for sending and receiving data via an Ethernet-based communications link or network. In another example, communications interface 124 can include a Wi-Fi transceiver for communicating via a wireless communications network or cellular or mobile phone communications transceivers.

Dressing with Lightguide

Referring to FIGS. 5-15 and 17, various embodiments of a lightguide dressing 200 and the therapy device 102 are shown. In some embodiments, any of the embodiments of the lightguide dressing 200 and the therapy device 102 described herein are usable with the NPWT system 100 as described in greater detail above with reference to FIGS. 1-4. In some embodiments, the lightguide dressing 200 and the therapy device 102 as described herein are provided as a system for providing NPWT in combination with phototherapy to a wound.

Figure 5:
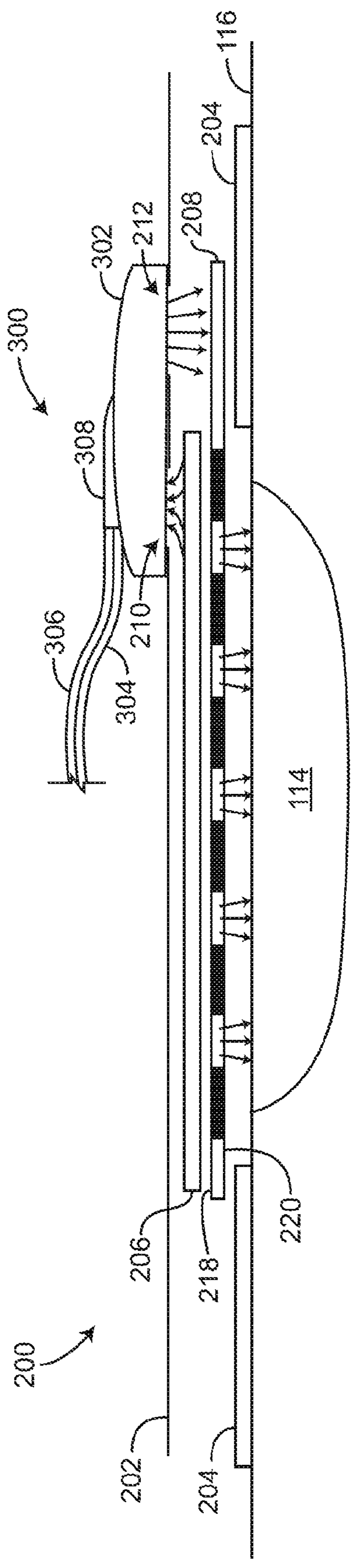
FIG. 5 is sectional view of a lightguide dressing, according to some embodiments.

Referring particularly to FIG. 5, a lightguide dressing 200 (e.g., a wound dressing, a NPWT dressing, etc.) is shown, according to some embodiments. The lightguide dressing 200 is configured to facilitate NPWT in addition to phototherapy for a wound 114 that the lightguide dressing 200 covers. In some embodiments, the lightguide dressing 200 is a dual-purpose dressing to facilitate phototherapy and NPWT to facilitate healing and/or disinfection of the wound 114.

The lightguide dressing 200 includes a drape 202, a manifold layer 206, a lightguide 208, and a skin interface layer 204, according to some embodiments. In some embodiments, the skin interface layer 204 is configured to directly contact, abut, engage, etc., an exterior surface of the patient's skin surrounding the wound 114 (e.g., periwound tissue 116). In some embodiments, the skin interface layer 204 is a Dermatac™ material that is manufactured by 3M™. In some embodiments, the skin interface layer 204 is configured to sealingly couple on one side with the periwound tissue 116, and on an opposite side with the drape 202. In some embodiments, the drape 202 and the skin interface layer 204 are configured to cooperatively define an inner volume that includes the wound 114 therewithin. In some embodiments, the skin interface layer 204 and the drape 202 are integrally formed and provided as a unitary member. In some embodiments, the skin interface layer 204 and the drape 202 are Dermatac™ Drape with V.A.C.® Granufoam™ as manufactured by 3M™.

In some embodiments, the manifold layer 206 is a foam layer that is configured to facilitate distribution of negative pressure throughout the inner volume defined by the drape 202 and the skin interface layer 204. The manifold layer 206 may also be a nonwoven or micro-replicated standoff film. In some embodiments, the manifold layer 206 is positioned within the inner volume (e.g., a sealed inner volume). In some embodiments, the manifold layer 206 is positioned directly below the drape 202 and an upper or top surface of the manifold layer 206 directly abuts or contacts an interior surface of the drape 202.

In some embodiments, the lightguide 208 is positioned directly below or beneath the manifold layer 206. In some embodiments, a bottom surface of the manifold layer 206 directly contacts or abuts an upper surface of the lightguide 208. In some embodiments, the lightguide 208 is positioned directly above the wound 114 between the manifold layer 206 and the wound 114. The lightguide 208 can be configured to receive light at a first portion, direct, diffuse, refract, etc., light through the lightguide 208, and emit light to the wound 114 for phototherapy.

The lightguide dressing 200 includes and/or is configured to interface or couple with a coupler assembly 300, according to some embodiments. In some embodiments, the coupler assembly 300 is configured to provide or facilitate delivery of negative pressure and light for the wound 114. The drape 202 includes a first opening 210 for drawing negative pressure (e.g., removing air from the inner volume defined by the drape 202 and the skin interface layer 204) and for providing light to the lightguide 208 for phototherapy. In this way, the coupler assembly 300 can function as a dual purpose coupler to both draw a negative pressure at the lightguide dressing 200 for NPWT, and also to provide or emit light to the lightguide 208 for phototherapy of the wound 114. In some embodiments, the coupler assembly 300 is adhered with the lightguide dressing 200 using a lightguide adhesive that is configured to transfer light through. In some embodiments, the lightguide 208 is provided as a coating or layer of adhesive that guides light. In some embodiments, the lightguide 208 is provided as a layer of adhesive that is sandwiched between film layers (e.g., transparent or translucent film layers).

In some embodiments, the drape 202 includes a first opening 210 and a second opening 212 with which the coupler assembly 300 is operably coupled. In some embodiments, the coupler assembly 300 is configured to draw a negative pressure within the dressing by fluidly coupling with the inner volume of the drape 202 and the skin interface layer 204 through the first opening 210. In some embodiments, the coupler assembly 300 includes a coupler 302, a connector 308, and a first tubular member 304 and a second tubular member 306 (e.g., tubes, conduits, pipes, lines, etc.).

In some embodiments, the coupler 302 is configured to fluidly couple the inner volume of the lightguide dressing 200 with the first tubular member 304 via the first opening 210 for drawing a negative pressure at the lightguide dressing 200. Specifically, the first tubular member 304 can be fluidly coupled with a NPWT device (e.g., therapy device 102) that includes a pump for drawing a negative pressure at the inner volume of the lightguide dressing 200. In some embodiments, the first tubular member 304 and the second tubular member 306 define fluid flow paths or light paths and are provided as a dual function conduit. In some embodiments, the first tubular member 304 is a flexible member. In some embodiments, the first tubular member 304 is an elongated member with a hollow center for drawing a negative pressure at the inner volume of the lightguide dressing 200 and for drawing exuded wound fluid from the inner volume of the lightguide dressing 200.

In some embodiments, the first opening 210 is positioned above a corresponding portion of the manifold layer 206 so that a direct path is formed between the first opening 210 and the manifold layer 206. The NPWT device may operate to draw a negative pressure at the inner volume of the lightguide dressing 200 via a fluid path defined between the NPWT device and the inner volume of the lightguide dressing 200 along the first tubular member 304, the connector 308, the coupler 302 (or internal channels thereof), and the first opening 210.

Similarly, the second opening 212 can be positioned above an upper surface 218 of the lightguide 208, according to some embodiments. In some embodiments, a direct path is defined between the second opening 212 and the upper surface 218 of the lightguide 208 so that light can be emitted from the second opening 212 to the upper surface 218 of the lightguide 208. In some embodiments, the second tubular member 306 is a light conduit (e.g., a fiber-optic cable) configured to receive light at a first end (e.g., at the NPWT device), and guide the light through the second tubular member 306, the connector 308, and internal channels (e.g., fiber optic channels) of the coupler 302 so that the light is emitted at an opposite end of the light conduit (e.g., at the second opening 212) to the upper surface 218 of the lightguide 208. In some embodiments, the lightguide 208 is configured to receive the light through the upper surface 218 (e.g., a first surface), guide the light through an interior of the lightguide 208, and emit the light out of the lightguide 208 (e.g., diffracted light) to the wound 114 through a bottom surface 220 of the lightguide 208. In some embodiments, a portion of the upper surface 218 of the lightguide 208 is directly below the second opening 212 and at least a portion of the bottom surface 220 of the lightguide 208 is directly above the wound 114 so that light can be received at the upper surface 218, transferred through the lightguide 208 and emitted from the bottom surface 220 to the wound 114. In some embodiments, the bottom surface 220, or a wound-facing surface of any other components of any of the dressings described herein for providing photo therapy and NPWT are coated with a photosensitizing agent. When the bottom surface 220 or the wound-facing surface of the dressing contacts the wound 114, the photosensitizing agent may be absorbed into the wound 114 to improve an efficacy of phototherapy.

In some embodiments, the lightguide 208 is provided as multiple layers of optical film that are configured to filter or enhance light that is provided to the interior of the lightguide dressing 200 via the second tubular member 306 and the coupler 302. For example, the light source that provides light to the lightguide 208 may be configured to emit visible light towards the multi-layered optical film lightguide and the multi-layered optical film lightguide can be configured to filter out certain wavelengths that are undesired so that only a specific wavelength of light (e.g., blue light, red light, IR light, near IR light, light having a wavelength of 400 to 450 nanometers, etc.) is provided to the wound 114. Advantageously, providing the lightguide 208 as multi-layered optical films can facilitate using a less precise light source (e.g., a visible light source), which is then transformed into appropriate wavelength of light to achieve desired phototherapy results.

Figure 6:
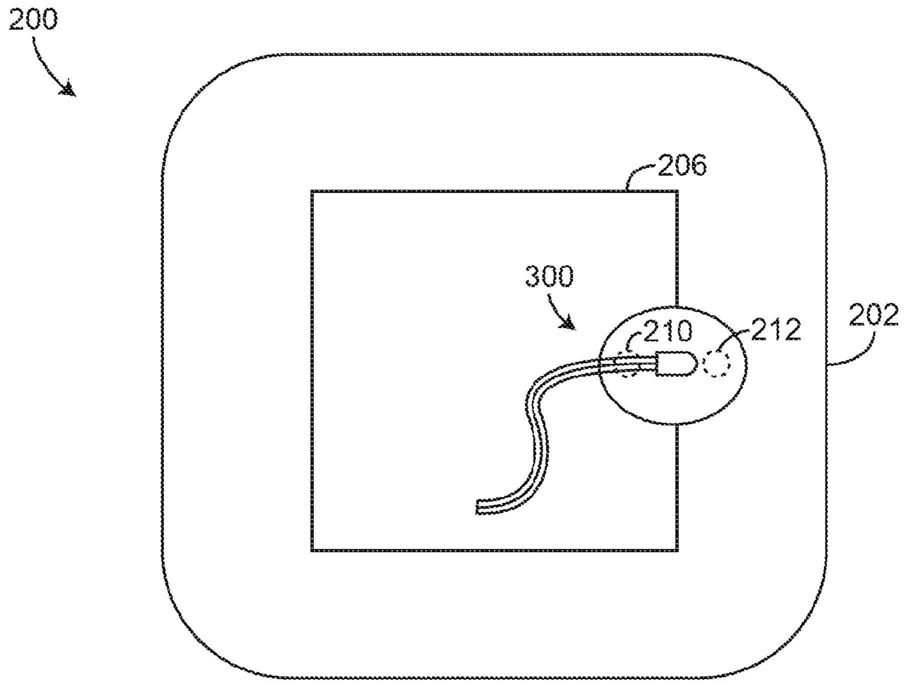
FIG. 6 is a top view of a lightguide dressing, according to some embodiments.

Referring particularly to FIG. 6, a top view of the lightguide dressing 200 is shown, according to some embodiments. In some embodiments, the coupler assembly 300 is positioned on an edge of the manifold layer 206 so that the second opening 212 can access the lightguide 208, and so that the first opening 210 can access the manifold layer 206 (e.g., for providing light for disinfection and for drawing negative pressure within the lightguide dressing 200, respectively).

Figure 7:
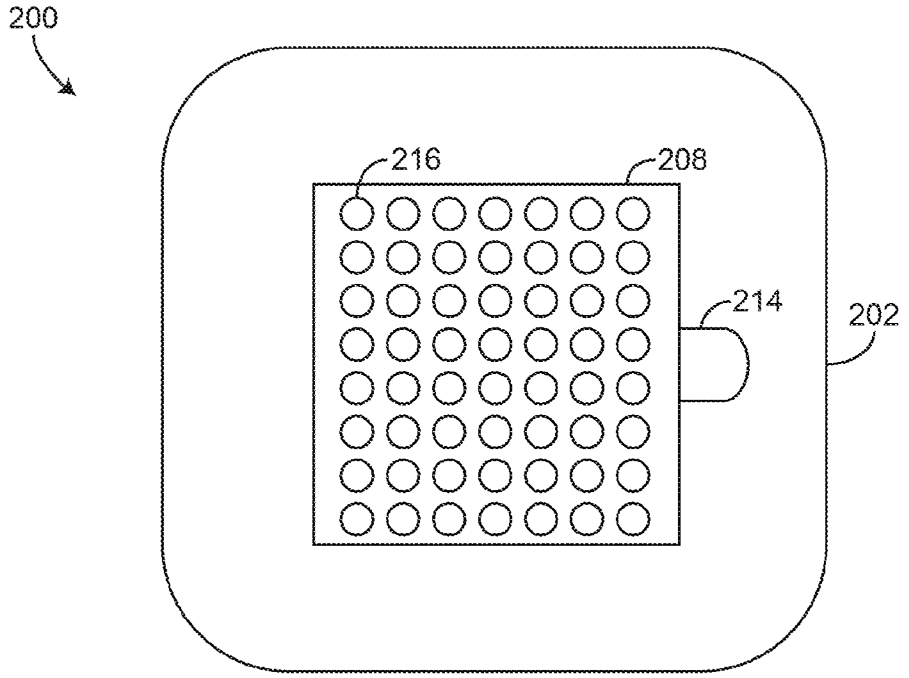
FIG. 7 is a bottom view of the lightguide dressing of FIG. 6, according to some embodiments.

Referring particularly to FIG. 7, a bottom view of the lightguide dressing 200 is shown, according to some embodiments. The bottom view of the lightguide dressing 200 shows the lightguide 208 and a tab, protrusion, flap, extending portion, arm, barb, body, elongated portion, tail, etc., shown as flap 214 extending outwardly from an edge or outer periphery of a body or main portion of the lightguide 208, according to some embodiments. In some embodiments, the flap 214 is configured to extend beyond the edge of the lightguide 208 so that the second opening 212 is over or above the flap 214. The flap 214 is configured to receive light emitted from the second opening 212 (e.g., via the coupler assembly 300 and the second tubular member 306), according to some embodiments. The flap 214 extends outwardly beyond an outer edge of the manifold layer 206 so that the second opening 212 can access the flap 214 and thereby provide light to the lightguide 208. As shown in FIGS. 5-9, the lightguide 208 includes an array of openings, apertures, through-holes, channels, etc., shown as openings 216. The openings 216 are configured to facilitate the drawing of negative pressure, fluid, etc., through the lightguide 208 when a negative pressure is drawn at the lightguide dressing 200, according to some embodiments. In some embodiments, the openings 216 are circular, elliptical, slits, etc., openings that extend through an entire thickness of the lightguide 208 so that fluid can be drawn from the wound 114 to the manifold layer 206 through the openings 216 during negative pressure operations, and/or so that fluid or photosensitizing agent can be provided to the wound 114 through the lightguide 208. In some embodiments, the openings 216 have a uniform size and/or shape along multiple dimensions of the array (e.g., along two dimensions of the array if the openings 216 are provided in a two-dimensional array). In some embodiments, the size and/or shape of the openings 216 varies along at least one dimension of the array. In some embodiments, the variation of the size and/or shape of the openings 216 along at least one of the directions of the array are configured to achieve specific parameters of the lightguide 208 for providing phototherapy (e.g., to achieve a specific light path through the lightguide 208, to achieve a desired refractive index, etc.).

Figure 8:
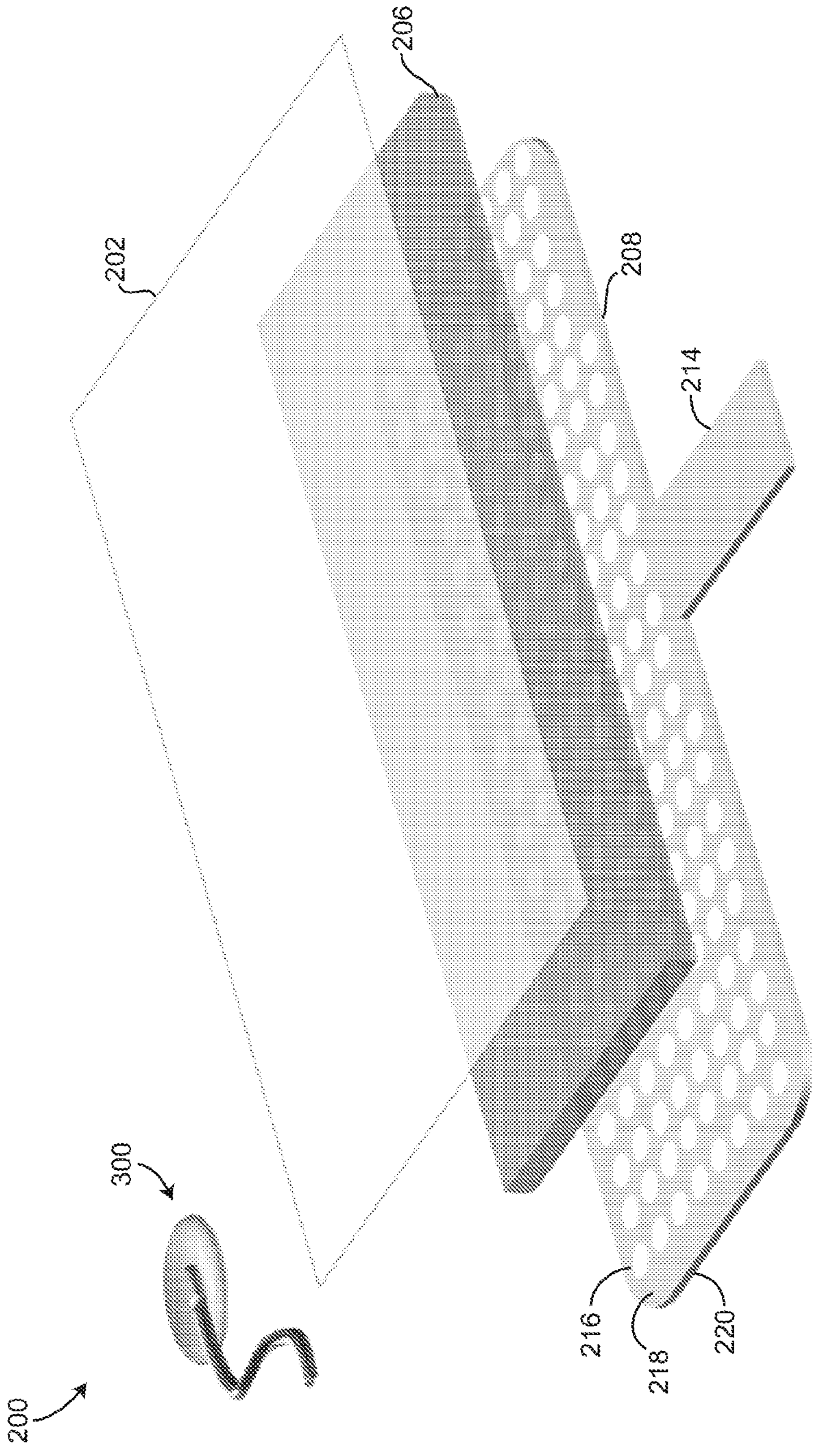
FIG. 8 is a perspective exploded view of a lightguide dressing including a tab for use with a coupler assembly, according to some embodiments.
Figure 9:
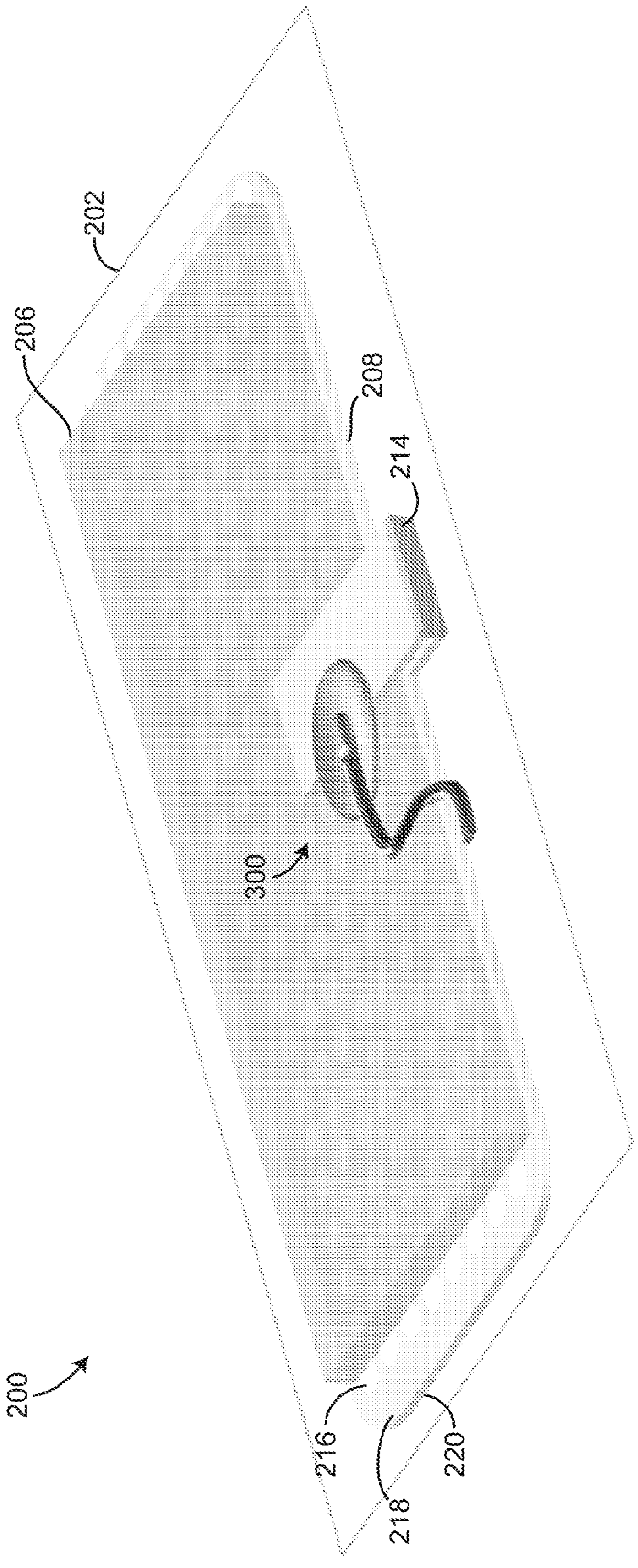
FIG. 9 is a perspective assembled view of the lightguide dressing and coupler assembly of FIG. 8, according to some embodiments.

Referring particularly to FIGS. 8-9, a perspective view of another embodiment of the lightguide dressing 200 is shown, according to some embodiments. The lightguide dressing 200 may be provided as a cut-to-shape design so that the lightguide 208 and the manifold layer 206 can be cut to a particular size and shape as desired by a user or caregiver, according to some embodiments. In some embodiments, the flap 214 is configured to wrap around the manifold layer 206 so that the flap 214 rests on top of the manifold layer 206 as shown in FIG. 9. The coupler assembly 300 is provided on top of the flap 214, above the manifold layer 206 and on an exterior surface of the drape 202 so that the coupler assembly 300 facilitates drawing negative pressure at the lightguide dressing 200 and also providing light to the lightguide 208 for disinfection. The coupler assembly 300 can be positioned on the exterior or outer surface of the drape 202 and above an edge of the flap 214 so that the first opening 210 and the second opening 212 are above the manifold layer 206 and the flap 214, respectively, according to some embodiments.

Figure 10:
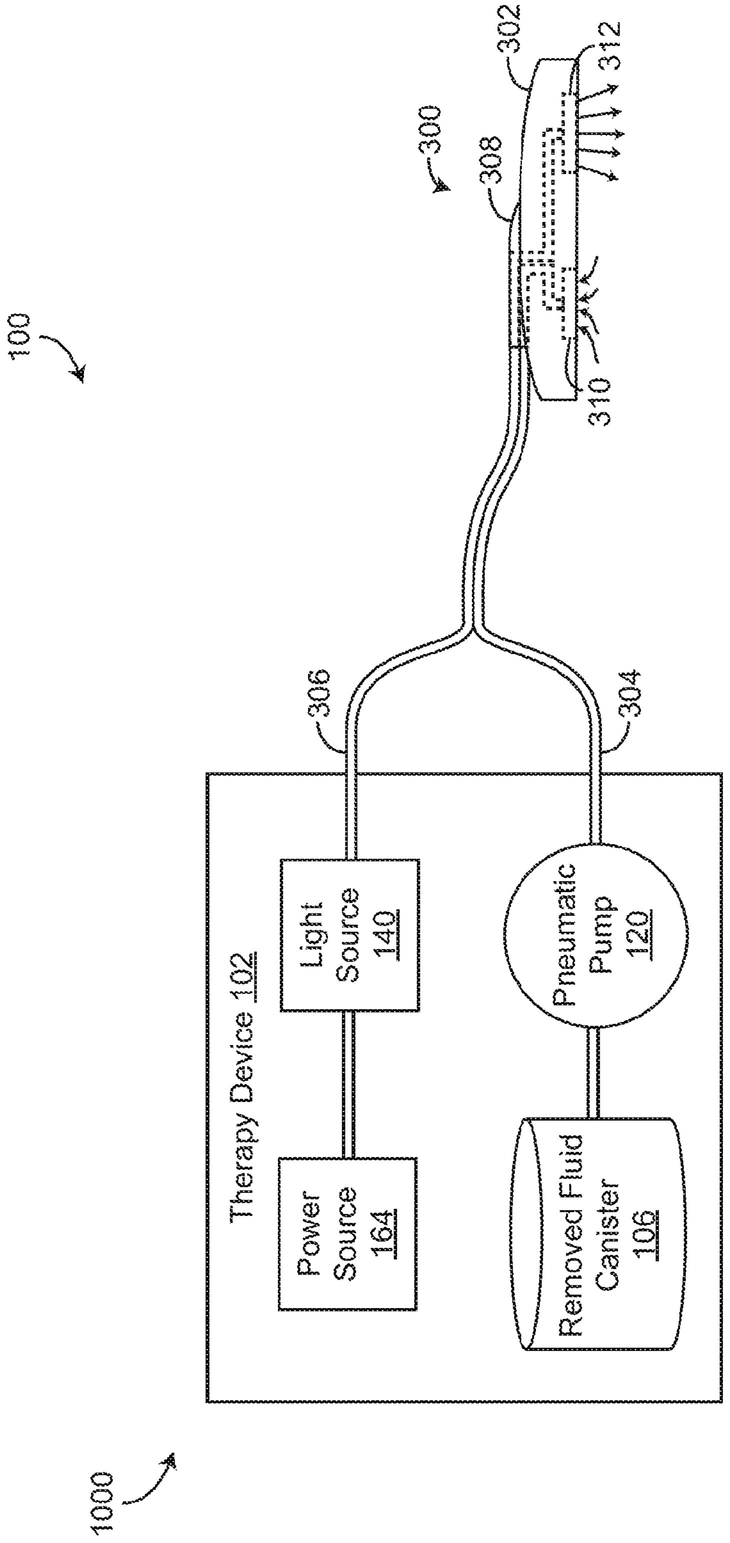
FIG. 10 is a block diagram of a therapy device and a coupler assembly for a lightguide dressing with a light source provided within the therapy device, according to some embodiments.

Referring particularly to FIG. 10, a diagram 1000 of the coupler assembly 300 and the therapy device 102 is shown, according to some embodiments. In some embodiments, the coupler assembly 300 as shown in FIG. 10 is the same as the coupler assembly 300 described in greater detail above with reference to FIGS. 6-9. In some embodiments, the coupler assembly 300 includes the first tubular member 304 and the second tubular member 306. In some embodiments, the first tubular member 304 is fluidly coupled with a first inlet/outlet 310 of the coupler 302 at a first end or is fluidly coupled at the first end with an internal channel of the coupler 302 that fluidly couples with the first inlet/outlet 310. In some embodiments, the first tubular member 304 is configured to couple at a second or distal end (e.g., an end of the first tubular member 304 that is opposite the end of the first tubular member 304 that fluidly couples with the first opening 210) with the pneumatic pump 120 of the therapy device 102 for drawing a negative pressure at the lightguide dressing 200. In some embodiments, the first inlet/outlet is configured to fluidly couple with an interior of the lightguide dressing 200 via the first opening 210 of the drape 202. In some embodiments, the second tubular member 306 (e.g., the fiber optic cable or cord) is configured to couple with a second inlet/outlet 312 of the coupler assembly 300 at a first end. In some embodiments, the second tubular member 306 couples, at the first end, with an internal channel of the coupler 302 that couples with the second inlet/outlet 312. In some embodiments, the second inlet/outlet 312 fluidly couples with the interior of the lightguide dressing 200 via the second opening 212 of the drape 202. In some embodiments, a second end of the second tubular member 306 is coupled with (e.g., electromagnetically coupled) a light source 140 so that light emitted by the light source 140 is transferred through the second tubular member 306 and emitted out of the second inlet/outlet 312 (e.g., to the lightguide 208). FIG. 10 shows an embodiment where two tubular members (e.g., the first tubular member 304 and the second tubular member 306) are used to draw a negative pressure at and to provide light (e.g., UV light) to the lightguide dressing 200. In some embodiments, the first tubular member 304 is a dual or multi-purpose fluid tube for providing instillation fluid to the lightguide dressing 200, drawing a negative pressure at the lightguide dressing 200, providing a photosensitizing agent (e.g., suspended in a liquid such as a saline solution) to the lightguide dressing 200, etc.

As shown in FIG. 10, the therapy device 102 can include a power source 164 (e.g., a battery, a capacitor, a Lithium Ion battery, etc.) that is configured to store and discharge electrical energy to the light source 140 for operation. In some embodiments, the power source 164 is a rechargeable power source that is on-board the therapy device 102. In some embodiments, the light source 140 is configured to draw power from a wall outlet, a permanent power source, a main power source, etc. In some embodiments, the therapy device 102 is configured to transition between the power source 164 and a main power source based on availability of the main power source. When the main power source is available, the therapy device 102 can consume electrical energy from the main power source (e.g., to power the light source 140, the pneumatic pump 120, the instillation pump 122, or any other electrical or electronic component of the therapy device 102), according to some embodiments. In some embodiments, the power source 164 is configured to charge when the therapy device 102 is electrically coupled with the main power source so that if connection between the therapy device 102 and the main power source fails (e.g., the therapy device 102 is unplugged from a wall outlet), the therapy device 102 can use electrical energy provided by the power source 164 for operation of the light source 140, the pneumatic pump 120, the instillation pump 122, etc. In some embodiments, the light source 140 includes one or more light emitting diodes (LEDs) configured to emit light (e.g., UV light) having a desired wavelength or frequency. In some embodiments, the light source 140 includes an LED that is operationally adjustable to emit light having the desired wavelength or frequency. In some embodiments, the light source 140 includes an array of multiple LEDs, each of which are configured to emit light having a predetermined wavelength or frequency. In some embodiments, the therapy device 102 may actuate one or more of the LEDs of the array to provide light having the desired wavelength or frequency. For example, a first LED may be actuated to provide light to the lightguide dressing 200 having a first wavelength or frequency, or a second LED may be actuated to provide light to the lightguide dressing 200 having a second wavelength or frequency, according to some embodiments.

Figure 11:
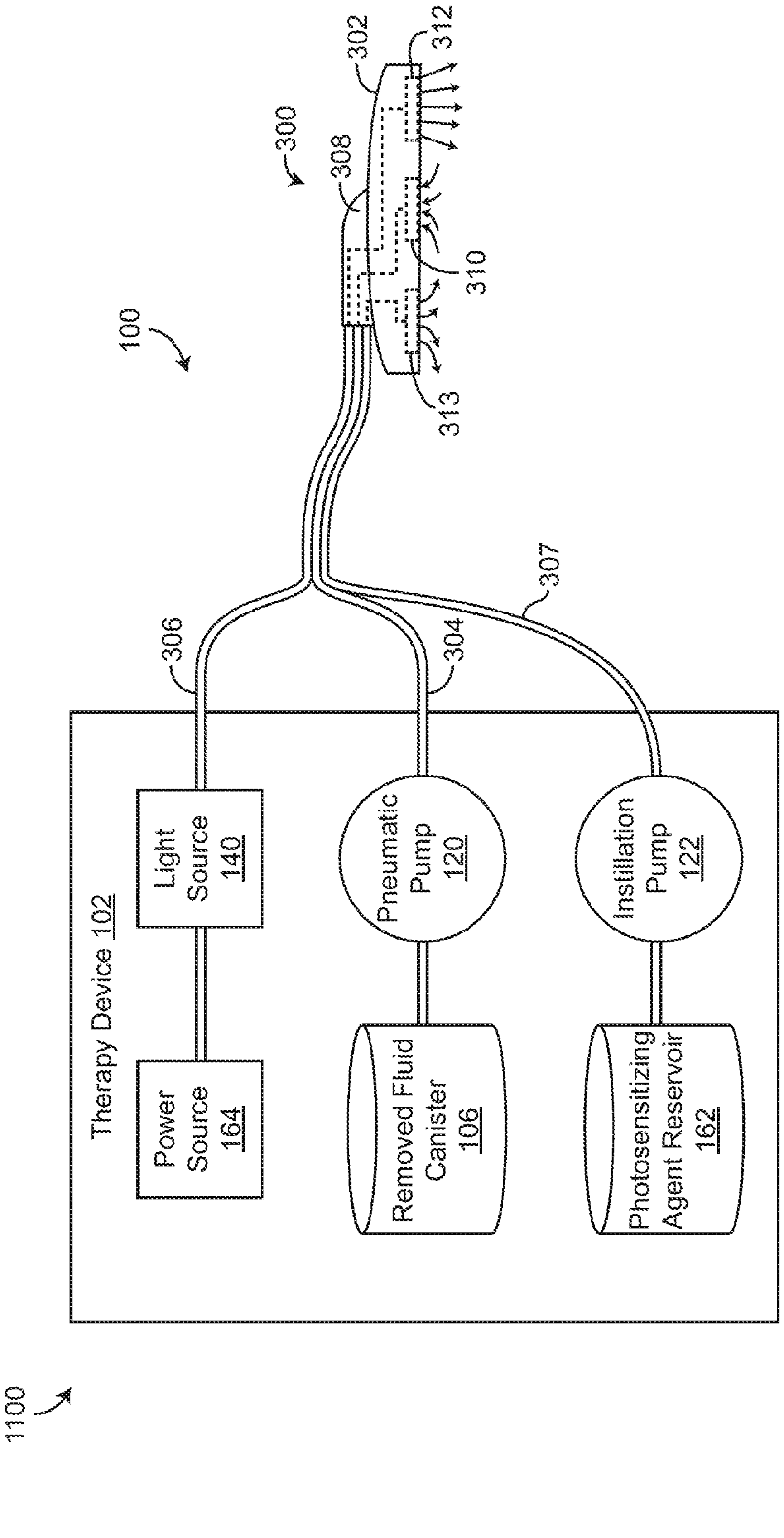
FIG. 11 is a block diagram of a therapy device and a coupler assembly for a lightguide dressing with a light source provided within the therapy device, with the therapy device configured to provide a photosensitizing agent to the lightguide dressing, according to some embodiments.

Referring particularly to FIG. 11, a diagram 1100 of the coupler assembly 300 and the therapy device 102 is shown, according to some embodiments. In some embodiments, the coupler assembly 300 as shown in FIG. 11 is similar to the coupler 300 as described in greater detail above with reference to FIGS. 6-10 but is configured for use with three tubular members. Specifically, the coupler assembly 300 is configured for use with the first tubular member 304, the second tubular member 306, and a third tubular member 307. The third tubular member 307 is configured to fluidly couple with a third inlet/outlet 313 of the coupler 302 for providing instillation fluid to an interior of the lightguide dressing 200 (e.g., at a first end), according to some embodiments. In some embodiments, the third tubular member 307 is configured to fluidly couple at an opposite end (e.g., a second end) with the instillation pump 122. In some embodiments, the instillation pump is configured to pump or drive fluid from a photosensitizing agent reservoir 162 to the interior of the lightguide dressing 200 through the third tubular member 307, the coupler 302, and the third inlet/outlet 213. In some embodiments, the third tubular member 307 is optional and the first tubular member 304 is configured to be selectably or transitionably fluidly coupled with the pneumatic pump 120 and the instillation pump 122 so that the first tubular member 304 can serve a dual-purpose (e.g., both for providing instillation fluid and/or a photosensitizing agent that may be suspended in the instillation fluid, and also for drawing a negative pressure at the lightguide dressing 200). In some embodiments, the pneumatic pump 120 and the instillation pump 122 are provided as a single pump that can operate to either push fluid into the lightguide dressing 200 (e.g., when fluidly coupled with the photosensitizing agent reservoir 162) or to draw fluid from the lightguide dressing 200 (e.g., when fluidly coupled with the removed fluid canister 106).

Figure 12:
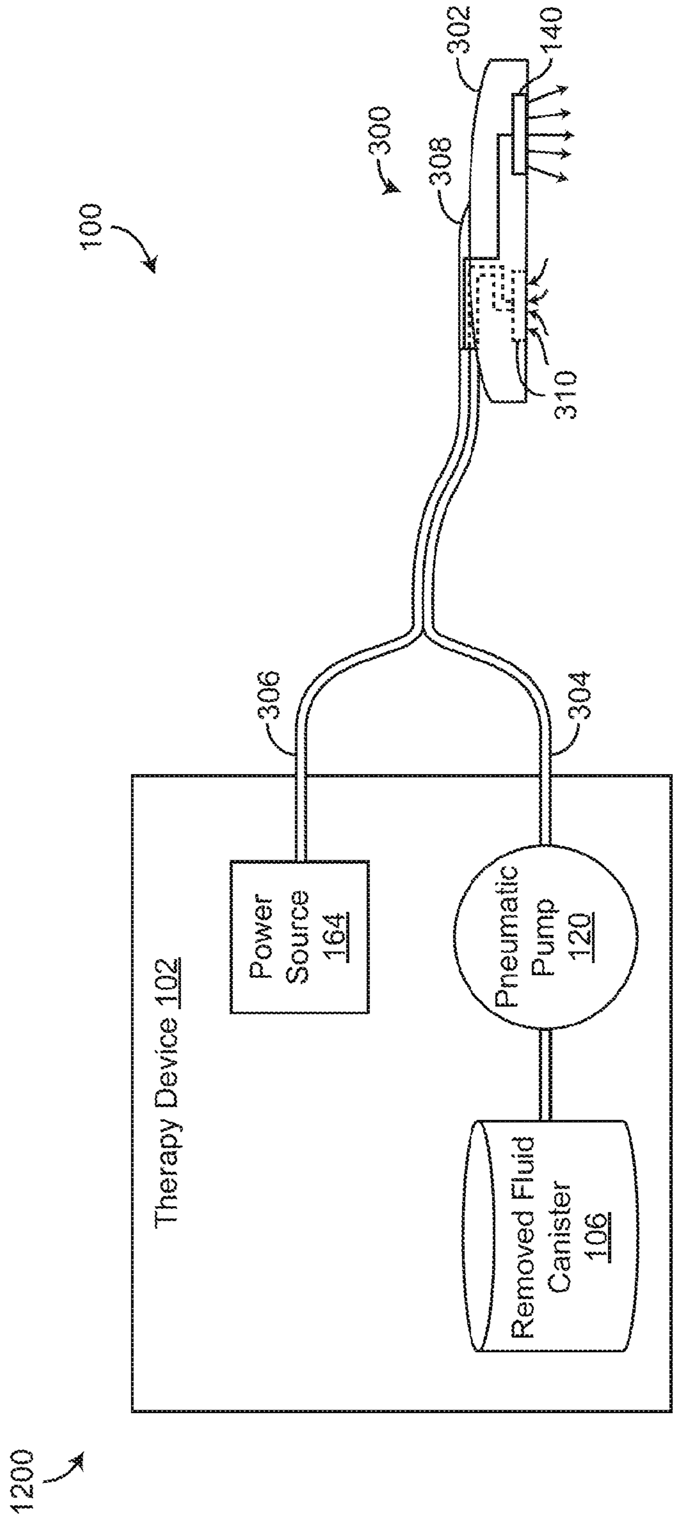
FIG. 12 is a block diagram of a therapy device and a coupler assembly for a lightguide dressing with a light source provided at the coupler assembly, according to some embodiments.

Referring particularly to FIG. 12, a diagram 1200 of the coupler assembly 300 and the therapy device 102 is shown, according to some embodiments. In some embodiments, the light source 140 is provided within the coupler 302 and is configured to emit light having a desired wavelength or frequency out of the coupler 302 to the lightguide 208 (e.g., via the second opening 212 of the drape 202). The light source 140 can be embedded within the coupler 302 and receive power from the power source 164 via the second tubular member 306. Specifically, the second tubular member 306 can be provided as an electrical cord or may include a conductor therewithin for transferring electrical energy from the power source 164 to the light source 140, according to some embodiments. In some embodiments, the coupler 302 may include the light source 140 therewithin, and may also be configured to fluidly coupled with the pneumatic pump 120 and the instillation pump 122 (e.g., via the first tubular member 304 and the third tubular member 307). In this way, the embodiments shown in FIGS. 11 and 12 may be combined so that photosensitizing agent can be provided to the interior of the lightguide dressing 200.

Figure 13:
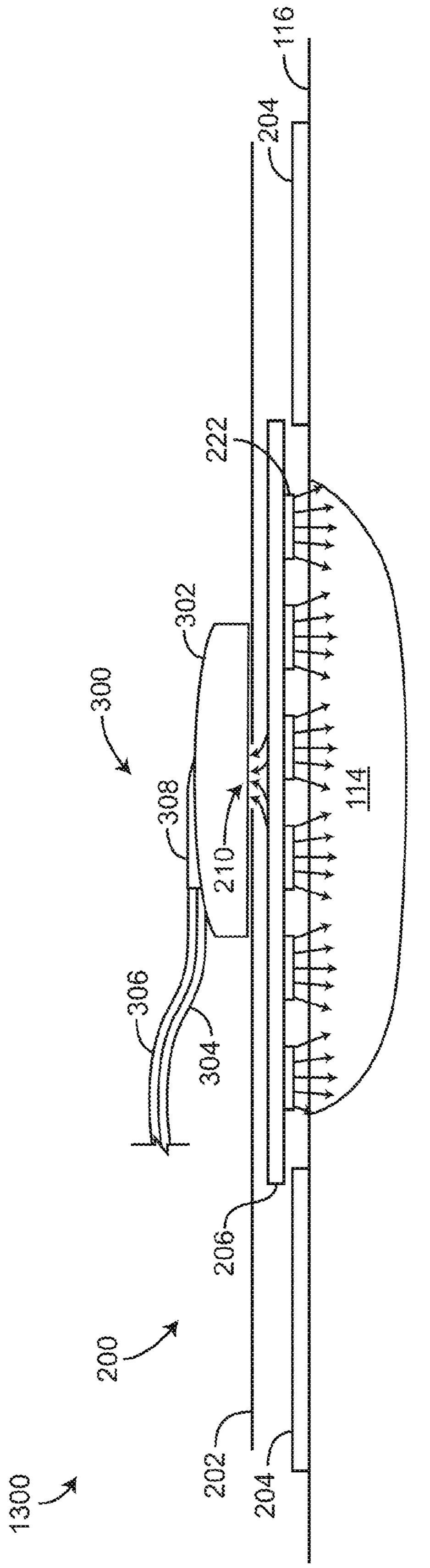
FIG. 13 is a sectional view of a lightguide dressing including one or more light sources provided on a manifold layer of the lightguide dressing, according to some embodiments.
Figure 14:
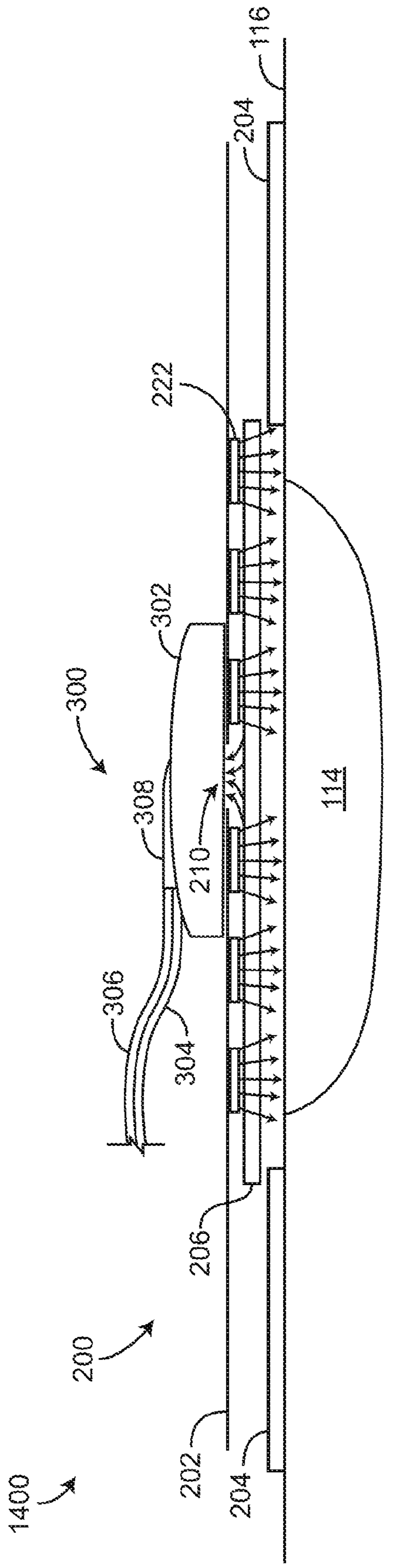
FIG. 14 is a sectional view of a lightguide dressing including one or more light sources provided on a drape layer of the lightguide dressing, according to some embodiments.

Referring particularly to FIGS. 13 and 14, diagrams 1300 and 1400 show the lightguide dressing 200 having LEDs provided within the dressing, according to some embodiments. Diagram 1300 and 1400 show embodiments of the lightguide dressing 200 where the lightguide 208 is not used and instead LEDs are positioned to provide light directly to the wound 114, according to some embodiments. The lightguide dressing 200 can include an array of LEDs 222 that are positioned along an interior surface of the drape 202 and configured to emit light towards the wound 114, as shown in FIG. 14. In some embodiments, the array of LEDs 222 are configured to emit light through one or more openings or micro-openings of the manifold layer 206 to the wound 114. The lightguide dressing 200 can include the array of LEDs 222 positioned alone a wound-facing side of the manifold layer 206 or embedded within a bottom surface of the manifold layer 206, according to some embodiments. In some embodiments, positioning the array of LEDs 222 within the lightguide dressing 200 facilitates reducing a number of components of the lightguide dressing 200, namely, providing a dressing that is configured for use with both phototherapy and negative pressure wound therapy without requiring the additional component of a lightguide structure. In some embodiments, the LEDs 222 are organic LEDs (OLEDs).

In some embodiments, the LEDs 222 are used in combination with the lightguide 208. For example, the LEDs 222 can be positioned on a bottom side of the manifold layer 206 and configured to introduce light to the lightguide 208 at different positions along the lightguide 208. In some embodiments, using the lightguide 208 in combination with the LEDs 222 facilitates using a reduced number of LEDs 222 since the lightguide 208 may improve efficiency of the LEDs 222.

Micro-Replicated Structures

Figure 15:
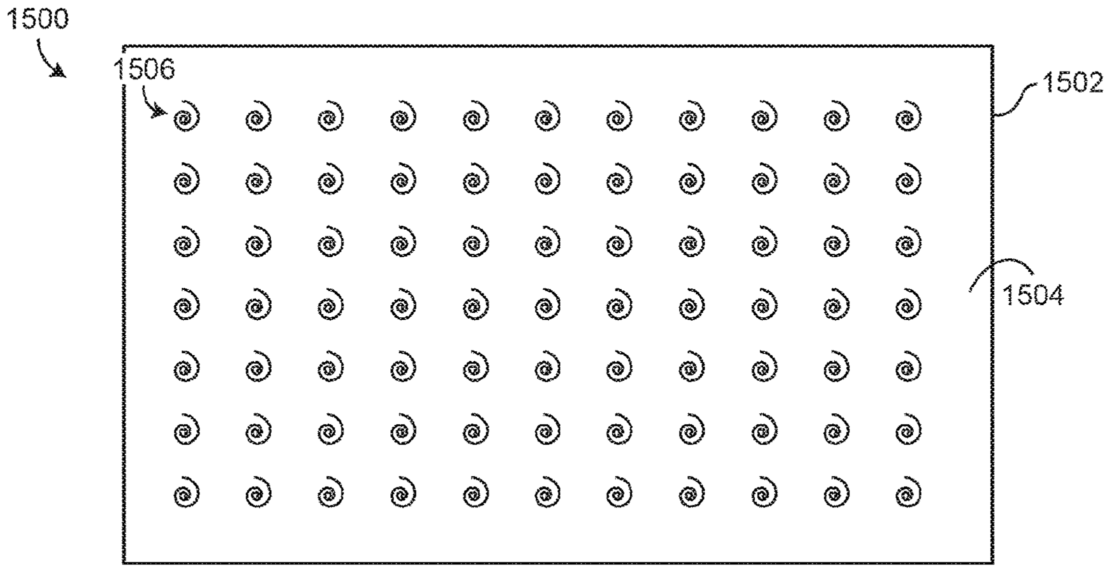
FIG. 15 is a bottom view of a wound-facing surface of a member of a dressing including one or more micro-replicated features, according to some embodiments.

Referring particularly to FIG. 15, a diagram 1500 of a wound facing surface 1504 of a dressing member 1502 is shown, according to some embodiments. The wound facing surface 1504 is a surface of the dressing member 1502 (e.g., the lightguide 208, the manifold layer 206, etc.) that is configured to abut, engage, directly contact, touch, etc., the wound 114, according to some embodiments. The dressing member 1502 can be any layer, member, element, etc., of a dressing that is configured to engage a wound (e.g., a wound interface layer). In some embodiments, the wound facing surface 1504 of the dressing member 1502 includes one or more microstructures 1506 that are arranged about the wound facing surface 1504. The microstructures 1506 can be any micro-replicated feature or geometry that is provided along the wound facing surface 1504 (e.g., in an array, in a pattern, etc.). The microstructures 1506 can be hook and latch features, channels, protrusions, biofilm breakers, light extractors, fluidic channels, etc., or any combination thereof. In some embodiments, the microstructures 1506 include any structural feature that protrudes from the wound facing surface 1504 towards the wound 114. In some embodiments, the microstructures 1506 can be configured to provide light (e.g., light that is diffracted or transferred through the dressing member 1502) to an interior of the wound 114 in various directions. In some embodiments, the microstructures 1506 can be configured to move as negative pressure is drawn at the wound 114 to thereby penetrate a biofilm of the wound 114 and facilitate deeper penetration of light provided using any of the dressings or techniques described herein.

In some embodiments, the wound facing surface 1504 includes an ultra-low index (ULI) film. In some embodiments, the dressing member 1502 is the lightguide 208. In some embodiments, the microstructures 1506 are extraction dots that are positioned across the wound facing surface 1504. In some embodiments, the microstructures 1506 are extraction dots with increased dot density and/or increased dot size with increased distance from a light injection edge (e.g., an edge or end of the lightguide 206 at which light is introduced)

Fluidic Lightguide

Figure 17:
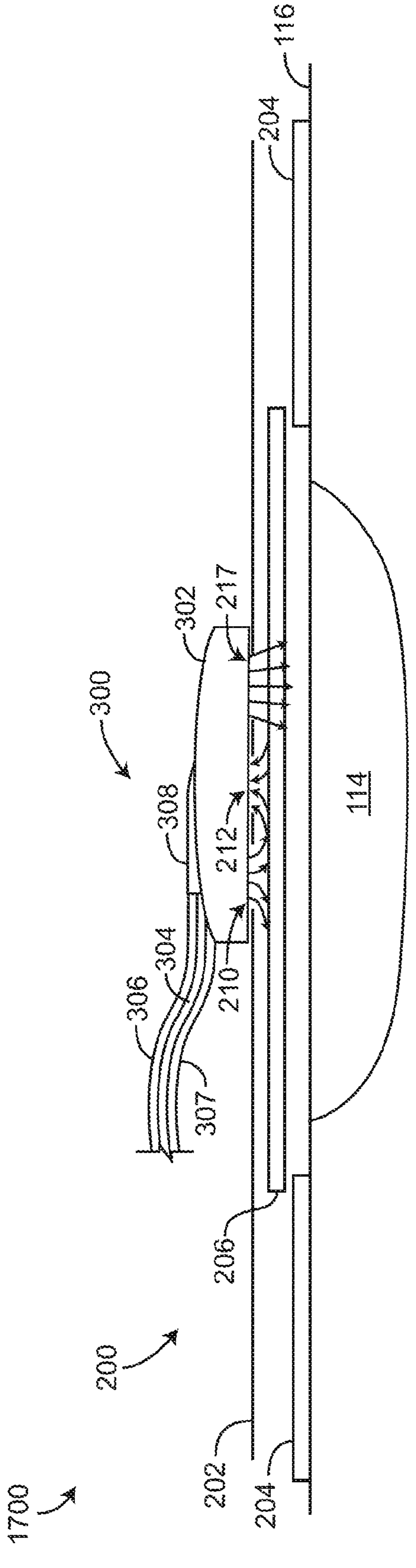
FIG. 17 is a sectional view of a lightguide dressing where a fluid is usable for a lightguide of the lightguide dressing, according to some embodiments.

Referring particularly to FIG. 17, a diagram 1700 of the lightguide dressing 200 with a fluidic lightguide is shown, according to some embodiments. In some embodiments, the lightguide dressing 200 includes the first opening 210, the second opening 212, and a third opening 217 in the drape 202. In some embodiments, the coupler assembly 300 is configured to couple with the first tubular member 304, the second tubular member 306, and the third tubular member 307. In some embodiments, each of the first tubular member 304, the second tubular member 306, and the third tubular member 307 fluidly coupled with a corresponding one of the first opening 210, the second opening 212, and the third opening 217. In some embodiments, the lightguide dressing 200 as shown in FIG. 17 is configured for flooding of an interior of the lightguide dressing 200 with a fluidic solution that functions as a lightguide to refract, diffuse, direct, etc., light throughout the fluidic solution into the wound 114. For example, the lightguide dressing 200 as shown in FIG. 17 may be coupled with the therapy device 102 so that the therapy device 102 can provide instillation fluid that includes one or more additives to facilitate transmission of light through the fluid.

In some embodiments, once an interior of the lightguide dressing 200 is flooded with the fluid, the therapy device 102 can be operated to provide light (e.g., UV light) to the interior of the lightguide dressing 200 while the fluid is in the interior of the lightguide dressing 200 and functions as a lightguide for the light provided to the interior of the lightguide dressing 200. In some embodiments, the light is provided to the interior of the lightguide dressing 200 using the embodiment of the light source 140 shown in FIG. 10 where the light source 140 is provided at the therapy device 102 and the light is transferred to the interior of the lightguide dressing 200 through the second tubular member 306.

In some embodiments, the light is provided to the interior of the lightguide dressing 200 using the embodiment of the light source 140 shown in FIG. 11 where the light source 140 is positioned at the coupler assembly 300. In some embodiments, the light is provided to the interior of the lightguide dressing 200 through the fluid as it is provided to the interior of the lightguide dressing 200 through the third tubular member 307. For example, the light source 140 may be positioned at the therapy device 102 and configured to emit light into an interior of the third tubular member 307 so that the light is transferred through fluid or liquid in the interior of the third tubular member 307, and into the interior of the lightguide dressing 200 that is flooded with the fluid or liquid (e.g., to act as a lightguide).

In some embodiments, an interior or wound facing surface of the drape 202 is reflective so that light that is reflected, refracted, etc., within the interior of the lightguide dressing 200 is reflected back towards the wound 114 to facilitate improved efficiency of the phototherapy (e.g., reducing leakage of the light into surrounding environment). In some embodiments, providing a reflective inner surface of the drape 202 configures the lightguide dressing 200 and the wound 114 to form or define a recycling cavity so that light is maintained within the lightguide dressing 200 to improve efficiency of the light source (e.g., to reduce a required amount of energy of the light source 140).

Referring again to FIG. 17, the manifold layer 206 can be manufactured from lofted non-woven fibers to both guide light and to also function as a manifold layer. In some embodiments, a structured film or molded material can also be used as a combination light delivery and manifold layer. In some embodiments, such a construction is advantageous for tunneling wounds so that the manifold layer 206 can be packed into the wound 114 beneath the skin.

Combined NPWT and Phototherapy Process

Figure 16:
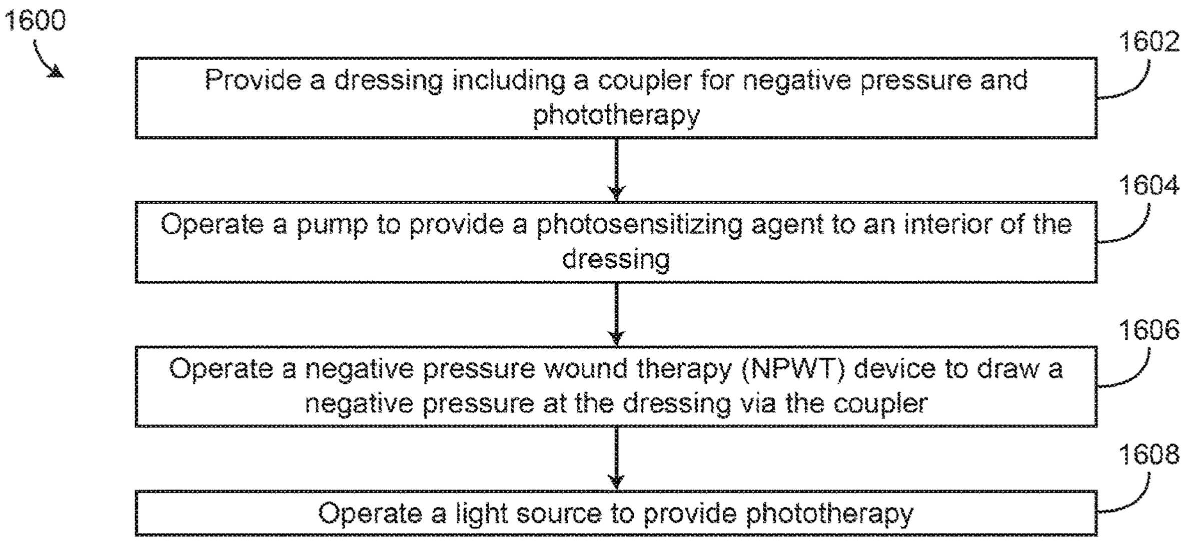
FIG. 16 is a flow diagram of a process for providing negative pressure wound therapy and phototherapy to a wound, according to some embodiments.

Referring particularly to FIG. 16, a process 1600 for providing phototherapy and negative pressure to a wound is shown, according to some embodiments. In some embodiments, process 1600 includes steps 1602-1608 and can be performed using the lightguide dressing 200 and/or the therapy device 102 as shown in any of the configurations or embodiments shown in FIGS. 1-14 and 17 or any combination thereof. In some embodiments, process 1600 is performed to facilitate healing and disinfection of a wound.

Process 1600 includes providing a dressing including a coupler for negative pressure and phototherapy (step 1602), according to some embodiments. In some embodiments, the dressing is the lightguide dressing 200 as described in greater detail above with reference to FIGS. 5-14 and 17. For example, the lightguide dressing 200 includes the coupler assembly 300 configured for use with one, two, or three tubular members. For example, the dressing provided in step 1602 may be the embodiment of the lightguide dressing 200 shown in FIGS. 5 and 10 where the light source 140 is provided within the therapy device 102 and light for disinfection or phototherapy can be provided to the interior of the lightguide dressing 200 (e.g., through the lightguide 208) via a fiber optic cable. In some embodiments, step 1602 includes providing the therapy device 102 and operably coupling the therapy device 102 with the dressing. In some embodiments, step 1602 includes sealing a drape of the dressing with periwound tissue so that the dressing is placed over a wound.

Process 1600 includes operating a pump to provide a photosensitizing agent to an interior of the dressing (step 1604), according to some embodiments. In some embodiments, step 1604 includes performing the instillation pump 122 (e.g., shown in FIG. 11) to provide the photosensitizing agent to the interior of the dressing. In some embodiments, the photosensitizing agent is suspended in a fluid so that the photosensitizing agent can be provided to the interior of the dressing through a tubular member that fluidly couples with the pump at one and, and fluidly couples with the interior of the dressing at an opposite end. In some embodiments, the photosensitizing agent includes Methylene blue or O-toluidine blue. In some embodiments, interior surfaces of the wound over which the dressing is placed are coated with the photosensitizing agent when the pump is operated to provide the photosensitizing agent to the interior of the dressing. In some embodiments, the photosensitizing agent is configured to increase an absorption of light (e.g., UV light) that is provided at step 1608 to facilitate the phototherapy and healing of the wound. In some embodiments, the photosensitizing agent is provided as particulate matter that is suspended in instillation fluid (e.g., a saline solution). In some embodiments, the photosensitizing agent is configured to increase an efficacy of the phototherapy that is performed by providing the light to the interior of the wound. In some embodiments, step 1604 is optional.

In some embodiments, step 1604 is performed manually by a clinician to provide the photosensitizing agent to the interior of the dressing. The clinician can perform step 1604 by injecting, pouring, or otherwise introducing the photosensitizing agent to the interior of the dressing, and then subsequently placing the dressing over the wound with the photosensitizing agent introduced.

Process 1600 includes operating a negative pressure wound therapy (NPWT) device to draw a negative pressure at the dressing via the coupler (step 1606), according to some embodiments. In some embodiments, step 1606 includes operating the therapy device 102 to draw the negative pressure at the dressing via the coupler. In some embodiments, step 1606 includes operating the pneumatic pump 120 to draw the negative pressure at the dressing via a tubular member (e.g., a dedicated tubular member for NPWT) and the coupler (e.g., the coupler assembly 300). In some embodiments, the NPWT device is the therapy device 102. In some embodiments, the NPWT device is operated to provide a static negative pressure or to provide a dynamic negative pressure. In some embodiments, a member of the dressing that is wound facing includes one or more microstructures (e.g., the microstructures 1506) and providing a dynamic or varying negative pressure at the dressing causes the microstructures to break a biofilm barrier. In some embodiments, providing the dynamic negative pressure causes the wound to vary in shape or geometry (e.g., adjusts, changes, or otherwise actuates surface topology of the wound 114 or of the wound bed), thereby exposing additional surfaces of the wound for phototherapy. In some embodiments, providing dynamic negative pressure includes varying the negative pressure (e.g., oscillating the negative pressure over time) between a first negative pressure and a second negative pressure. Oscillating the negative pressure over time may cause geometry of the wound 114 to change over time, thereby exposing additional tissue for the phototherapy.

Process 1600 includes operating a light source to provide phototherapy (step 1608), according to some embodiments. In some embodiments, step 1608 includes providing the light to the wound. In some embodiments, step 1608 includes operating a light source to provide light (e.g., UV light, light having a wavelength of 207 nanometers, red light, blue light, near infrared (IR) light, etc.) to the wound for phototherapy. In some embodiments, step 1608 includes operating the light source to provide a single wavelength of light to the wound. In some embodiments, step 1608 includes operating the light source to provide light at a single wavelength to the wound. In some embodiments, step 1608 includes operating the light source to provide light at a first wavelength over a first time, and to provide light at a second wavelength over a second time period. In some embodiments, step 1608 includes operating the light source to provide multiple streams of light having different wavelengths. Red or near-IR light may advantageously be used to induce biological effects that promote or facilitate healing of the wound, according to some embodiments. In some embodiments, blue light can be used to induce antibiotic sensitivity in antibiotic resistant organisms and/or to provide cytotoxic effects on microorganisms that are within the wound. In some embodiments, UVC light having a wavelength of 207 nanometers is used due to UVC light with a wavelength of 207 nanometers killing bacteria without apparent harm to human cells. The light source can be provided within the dressing (e.g., as shown in FIGS. 13-14), within the coupler (e.g., as shown in FIG. 12) or within the NPWT device (e.g., as shown in FIGS. 10-11), according to some embodiments.

It should be understood that steps 1604-1608 are not necessarily performed in subsequent order. For example, steps 1606-1608 can be performed at least partially concurrently or simultaneously so that negative pressure is provided to the wound while phototherapy is also provided to the wound. Providing negative pressure (e.g., dynamically or statically) may affect a geometry of the wound bed, thereby exposing different surfaces of the wound bed to the light provided during phototherapy, and thereby improving the efficacy of the phototherapy. Advantageously, the combination of NPWT and phototherapy may have a combined advantage of facilitating healing progression of the wound.

In some embodiments, step 1608 is performed in response to step 1604 and a pause or a time delay is performed prior to performing step 1606. For example, the photosensitizing agent can be provided to the interior of the dressing to thereby coat interior surfaces of the wound, and then the light source can be operated to provide phototherapy for a time duration (e.g., 5 minutes, 10 minutes, half an hour, etc.) prior to performing step 1606 and operating the NPWT device to draw the negative pressure at the wound. In some embodiments, the configuration of the lightguide or the specific photosensitizing agent used (e.g., in steps 1602 and 1604) is tailored or designed for use with a specific wavelength of the light that is provided during phototherapy. For example, if light having a wavelength substantially ranging from 400 to 450 nanometers is to be used in step 1608, a lightguide of the dressing as provided in step 1602 may have a specific refractive index (RI) configured for use with light having a wavelength from 400 to 450 nanometers.

Therapy Device Controller

Figure 18:
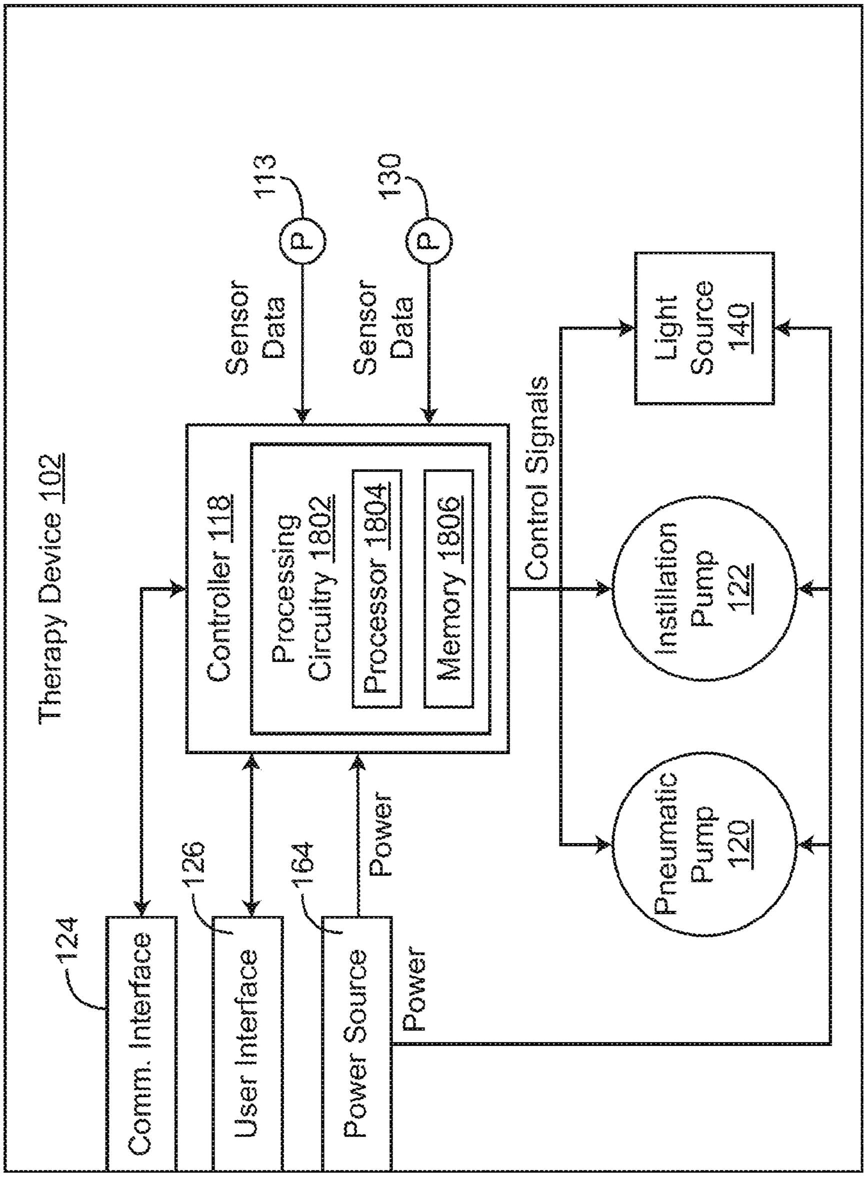
FIG. 18 is a block diagram of a therapy device configured to operate a pneumatic pump, an instillation pump, and a light source to provide negative pressure wound therapy (NPWT) and phototherapy, according to some embodiments.

Referring particularly to FIG. 18, a block diagram of the therapy device 102 configured to operate the pneumatic pump 120 (e.g., for NPWT), the instillation pump 122 (e.g., for providing instillation fluid, a saline solution, a solution including a photosensitizing agent, etc.), and the light source 140 (e.g., for phototherapy) is shown, according to some embodiments. In some embodiments, the power source 164 is configured to provide electrical power to any of the controller 118, the pneumatic pump 120, the instillation pump 122, or the light source 140. In some embodiments, the controller 118 is also configured to obtain sensor data from the pressure sensors 113 and 130. In some embodiments, the controller 118 is configured to generate control signals for the pneumatic pump 120, the instillation pump 122, and/or the light source 140 to provide NPWT and/or phototherapy to a patient's wound.

The controller 118 is shown to include processing circuitry 1802 including a processor 1804 and memory 1806. The processing circuitry 1802 can be communicably connected to the communications interface 124 such that the processing circuitry 1802 and the various components thereof can send and receive data via the communications interface 124. The processor 1804 can be implemented as a general purpose processor, an application specific integrated circuit (ASIC), one or more field programmable gate arrays (FPGAs), a group of processing components, or other suitable electronic processing components.

The memory 1806 (e.g., memory, memory unit, storage device, etc.) can include one or more devices (e.g., RAM, ROM, Flash memory, hard disk storage, etc.) for storing data and/or computer code for completing or facilitating the various processes, layers and modules described in the present application. The memory 1806 can be or include volatile memory or non-volatile memory. The memory 1806 can include database components, object code components, script components, or any other type of information structure for supporting the various activities and information structures described in the present application. According to some embodiments, the memory 1806 is communicably connected to the processor 1804 via the processing circuitry 1802 and includes computer code for executing (e.g., by the processing circuitry 1802 and/or the processor 1804) one or more processes described herein.

Hole Arrangement

Figure 19:
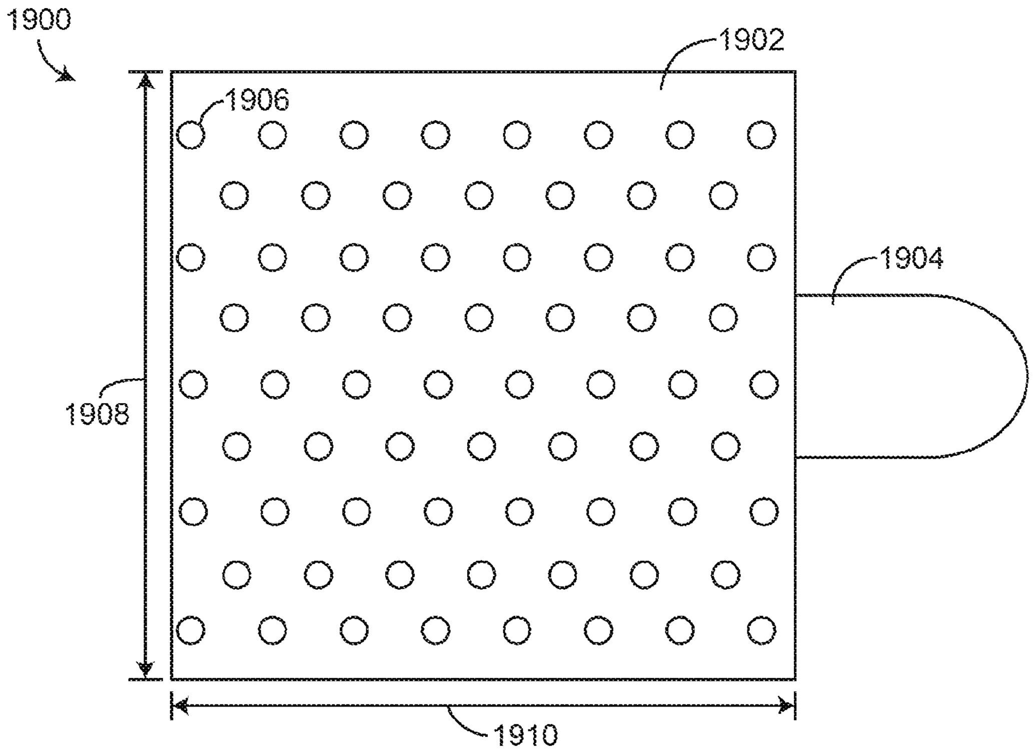
FIG. 19 is a top view of a lightguide, according to some embodiments.
Figure 20:
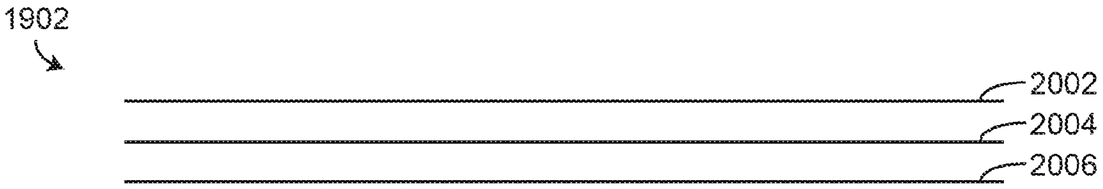
FIG. 20 is a side view of the lightguide of FIG. 19, according to some embodiments.

Referring to FIGS. 19-20, a lightguide 1900 is shown, according to some embodiments. In some embodiments, the lightguide 1900 is substantially the same or similar as the lightguide 208 as described in greater detail above with reference to at least FIGS. 5-15 and 17. FIG. 19 shows the lightguide 1900 including a body 1902 and a tab 1904. The tab 1904 may be the same as the flap 214. The body 1902 includes several arrays of holes 1906 that extend through the body 1902 and are arranged in a staggered pattern. The body 1902 of the lightguide 1900 is shown having a length 1908 and a width 1910. In some embodiments, the length 1908 and the width 1910 are equal dimensions so that the body 1902 is a square. In some embodiments, the length 1908 and the width 1910 are both five inches. In some embodiments, an edge of the body 1902 with which the 1904 is an injection edge through which light originates or is provided. As shown in FIG. 20, the body 1902 of the lightguide 1900 (or similarly, the entire lightguide 1900) may include a first silicone layer 2002, a second silicone layer 2006, and an adhesive layer 2004 positioned between the first silicone layer 2002 and the second silicone layer 2006. In some embodiments, the adhesive layer 2004 is a double-sided adhesive layer configured to adhere to both the first silicone layer 2002 and the second silicone layer 2006.

Light Transmission Tests

Figure 22:
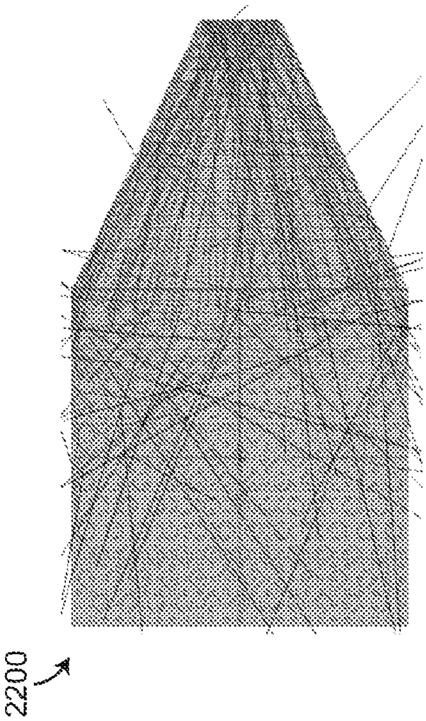
FIG. 22 is a diagram of the lightguide of FIG. 21 illustrating light paths as light propagates through the first lightguide, according to some embodiments.
Figure 21:
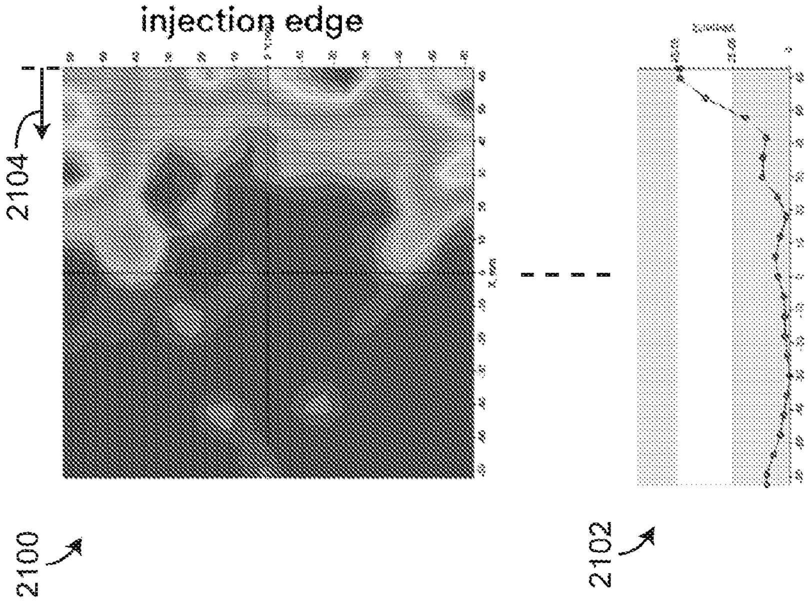
FIG. 21 is a diagram showing transmission of light through a first lightguide, according to some embodiments.

FIGS. 21-22 show results of a test to measure light transmission efficiency of a first embodiment of the lightguide 1900 where the holes 1906 have a diameter of 6 millimeters, according to some embodiments. FIG. 21 shows a diagram 2100 of the lightguide 1900 visually illustrating the transmission of light through the lightguide 1900 from the injection edge in direction 2104. A graph 2102 illustrates a power density (e.g., Watts per square millimeter) of the lightguide 1900 having 6 mm holes along an X-dimension of the lightguide 1900. As shown in FIG. 21, the power density of the light in the lightguide 1900 is high at the injection edge but quickly decreases. FIG. 22 is a diagram 2200 illustrating light paths of light transferring through the lightguide 1900 with 6 mm diameter holes. As shown in FIG. 22, when the lightguide 1900 has 6 mm diameter holes, the light path may be blocked by the through holes, leading to decreased efficiency.

Figure 23:
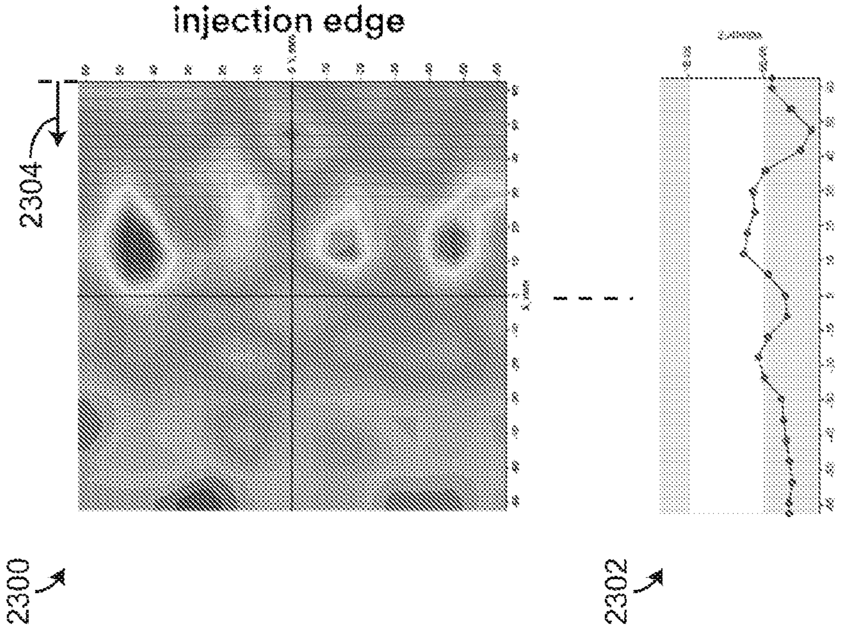
FIG. 23 is a diagram showing transmission of light through a second lightguide, according to some embodiments.

FIG. 23 shows results of a test to measure light transmission efficiency of a second embodiment of the lightguide 1900 where the holes 1906 have a diameter of 2 millimeters, according to some embodiments. FIG. 23 shows a diagram 2300 of the lightguide 1900 visually illustrating the transmission of light through the lightguide 1900 from the injection edge in direction 2304. A graph 2302 illustrates a power density (e.g., Watts per square millimeter) of the lightguide 1900 having 2 mm diameter holes along an X-dimension of the lightguide 1900. As shown in FIG. 23, the power density of the light in the lightguide 1900 is more distributed and even along the length of the lightguide 1900 than in FIGS. 21-22. The power density of the light in the lightguide 1900 results in a lightguide efficiency of 10%. Advantageously, reducing the size or diameter of the holes 1906 from 6 mm to 2 mm is shown to facilitate an improved transmission of light through the lightguide 1900.

Figure 24:
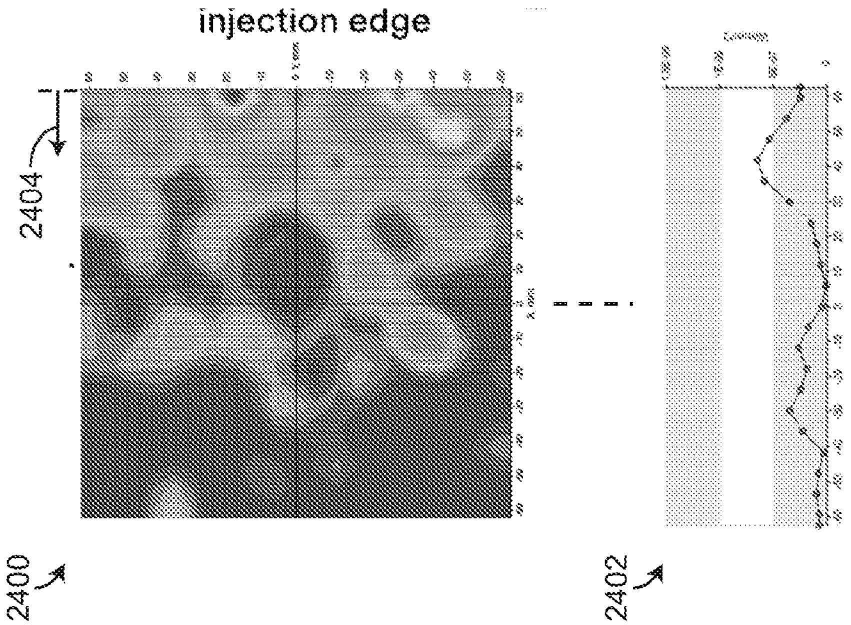
FIG. 24 is a diagram of the second lightguide of FIG. 23 illustrating light paths as light propagates through the second lightguide, according to some embodiments.

FIG. 24 shows results of a test to measure light transmission efficiency of a third embodiment of the lightguide 1900 where the holes 1906 have a diameter of 6 mm. FIG. 24 shows a diagram 2400 of the lightguide 1900 visually illustrating the transmission of light through the lightguide 1900 from the injection edge in direction 2404. A graph 2402 illustrates a power density (e.g., Watts per square millimeter) of the lightguide 1900 having 6 mm diameter holes along an X-dimension of the lightguide 1900. As shown in FIG. 24, the light path may be blocked by the 6 mm holes, thereby limiting efficiency of light transfer through the lightguide 1900.

Figure 26:
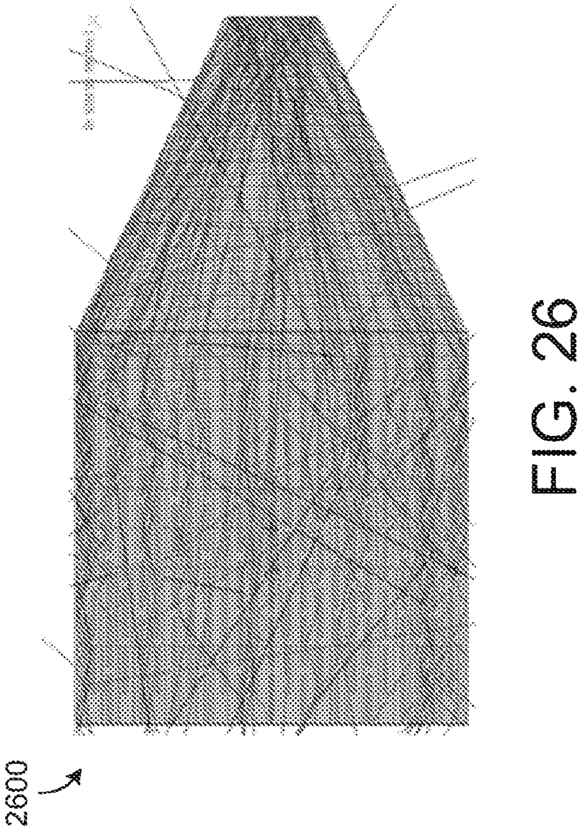
FIG. 26 is a diagram of the third lightguide of FIG. 25 illustrating light paths as light propagates through the second lightguide, according to some embodiments.
Figure 25:
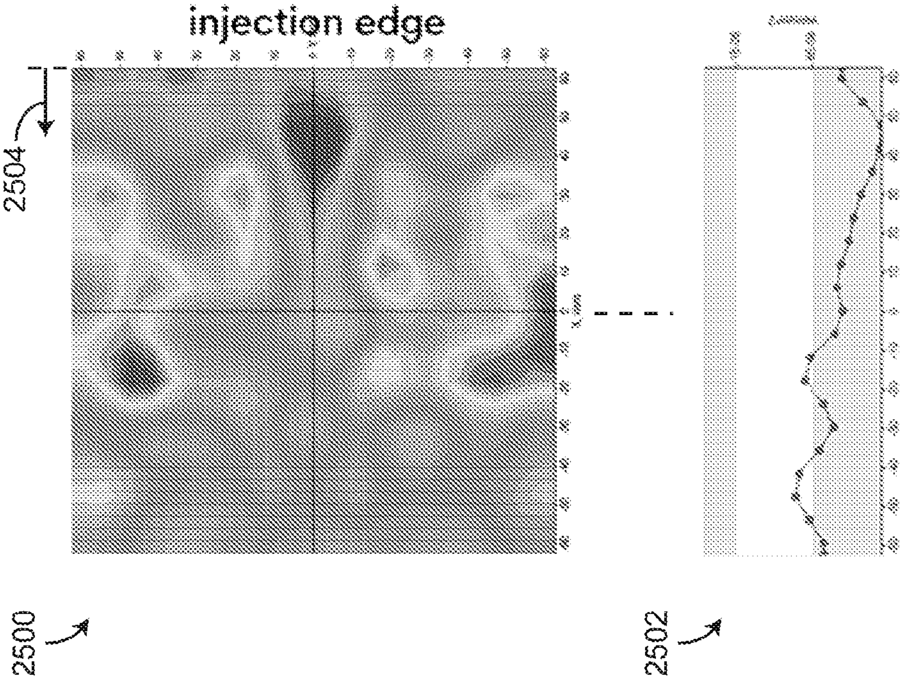
FIG. 25 is a diagram showing transmission of light through a third lightguide, according to some embodiments.

FIGS. 25-26 show results of a test to measure light transmission efficiency of a third embodiment of the lightguide 1900 where the holes 1906 have an elongated shape (e.g., elongated in a direction 2504 in which light is emitted into the lightguide 1900). The shape and size of the holes 1906 can be adjusted to optimize both uniformity of light transmission through the lightguide 1900 and efficiency of light transmission through the lightguide 1900. As shown in a diagram 2500, light is introduced to the lightguide 1900 along an injection edge in direction 2504. FIG. 25 includes a graph 2502 that illustrates power density of light in the lightguide 1900 along an X-direction of the lightguide 1900. As shown in FIG. 25, the elongated holes facilitate improved efficiency (approximately 10%) of the transfer of light through the lightguide 1900, and improved uniformity. FIG. 26 shows a diagram 2600 of light paths through the lightguide 1900 with elongated holes.

Hole Size and Arrangement

Figure 27:
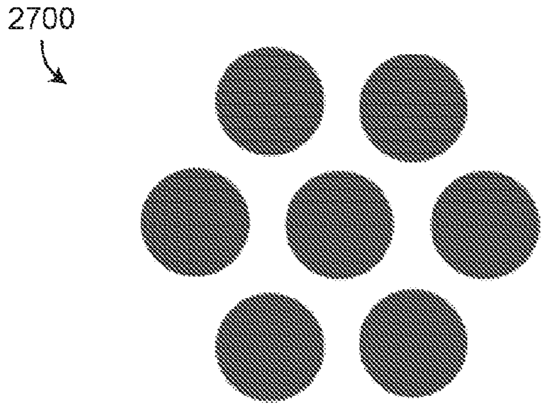
FIG. 27 is a diagram showing openings of a lightguide having a circular shape, according to some embodiments.
Figure 28:
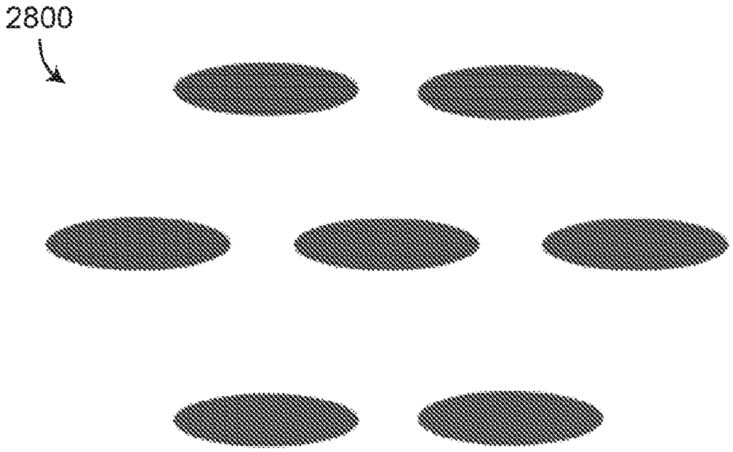
FIG. 28 is a diagram showing openings of a lightguide having an elliptical shape, according to some embodiments.

Referring to FIGS. 27-28, diagrams 2700 and 2800 illustrate different shapes and sizes of the holes 1906 according to various embodiments. FIG. 27 shows the holes 1906 having a circular shape, while FIG. 28 shows the holes 1906 having an elliptical shape. Using the elliptical shapes can increase a width wise dimension of the holes 1906 to facilitate improved efficiency of light transmission through the lightguide 1900. Referring to FIGS. 7 and 19, the holes 216 or 1906 may be arranged according to a rectangular pattern or a staggered pattern. In some embodiments, a rectangular pattern may facilitate improved transfer of light through the lightguide 1900 or 208.

Lightguide with Zones

Figure 29:
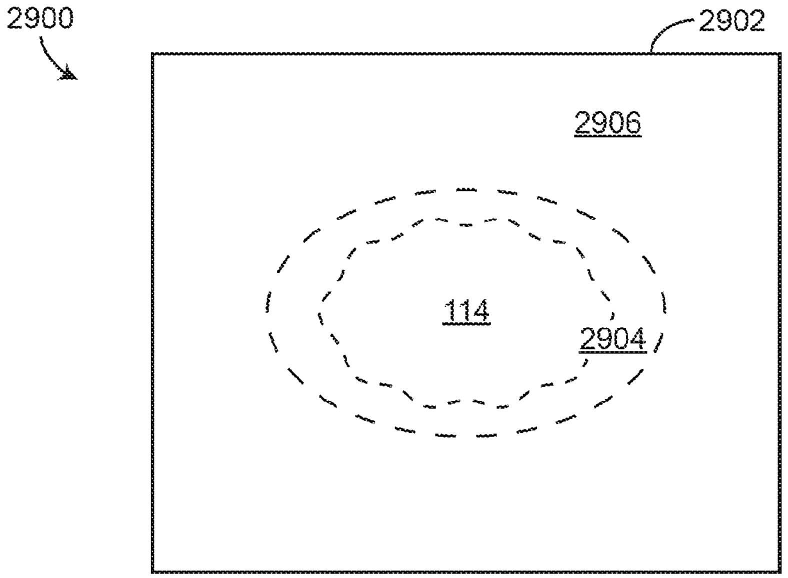
FIG. 29 is a diagram of a lightguide having different zones for providing different wavelengths or powers of light to different parts of a wound, according to some embodiments.
Figure 30:
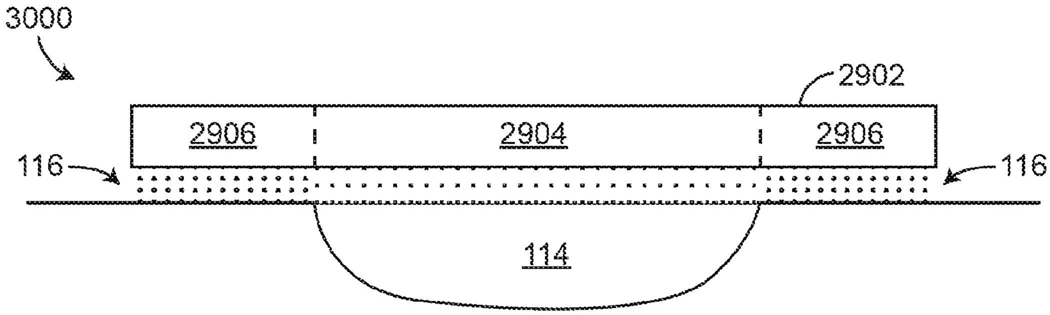
FIG. 30 is a side view of the lightguide of FIG. 29 illustrating the different wavelengths or powers of light that are provided to the different parts of the wound, according to some embodiments.

Referring to FIGS. 29 and 30, a lightguide 2902 for providing zoned lighting or phototherapy is shown, according to some embodiments. The lightguide 2902 can be used with the lightguide dressing 200 (e.g., in place of the lightguide 208). The lightguide 2902 may include any similar features to the lightguide 208 or the lightguide 1900 and may include various through holes or perforations so that negative pressure can be drawn through the lightguide 2902.

Referring particularly to FIG. 29, a diagram 2900 illustrates a top view of the lightguide 2902, according to some embodiments. The lightguide 2902 includes a first zone 2904 and a second zone 2906. The first zone 2904 and the second zone 2906 are configured to provide light to the wound 114 and/or the periwound tissue 114 (or to different parts of the wound 114) with different wavelengths or different power. For example, the first zone 2904 may be configured to provide light having a first wavelength, power, or intensity, etc., while the second zone 2906 provides light having a second wavelength, power, or intensity, etc. In some embodiments, the first zone 2904 is configured to provide light having the first wavelength, power, or intensity to the wound 114, while the second zone 2906 is configured to provide light having the second wavelength, power, or intensity to the periwound 116. Advantageously, providing light having different wavelengths to different parts of the wound 114 and the periwound 116 facilitates targeted healing or disinfection of the wound 114 and/or the periwound 116. For example, the periwound 116 may be configured to receive light having a wavelength of approximately 680 nanometers, while the wound 114 receives light having a different wavelength to facilitate perfusion of the wound 114 and the periwound 116.

In some embodiments, the first zone 2904 and the second zone 2906 are different materials or materials with different refractive indices so that light having different wavelengths or different powers are provided to the wound 114 and the periwound 116, respectively, or so that different wavelengths of light or different powers are provided to different portions of the wound 114 or different portions of the periwound 116.

In some embodiments, the wound 114 and/or the periwound 116 receive different wavelengths or powers of light depending on a refractive index of a type of tissue (e.g., skin, clean wound bed, biofilm, etc.). For example, the lightguide 2902 may include one or more sensors that are positioned about a bottom surface of the lightguide 2902 and are configured to detect a type of tissue that is proximate each sensor. In some embodiments, the lightguide 2902 includes the LEDs 222 positioned above or on a bottom surface of the lightguide 2902. The LEDs 222 can be configured to provide variable or controllable wavelength of light to the wound 114 and/or the periwound 116. In some embodiments, the controller 118 is configured to receive sensor data from the one or more sensors and operate the LEDs 222 to provide light having different wavelengths or different powers at the first zone 2904 and the second zone 2906 for the different types of tissue.

Lightguide Dressing with Camera

Figure 31:
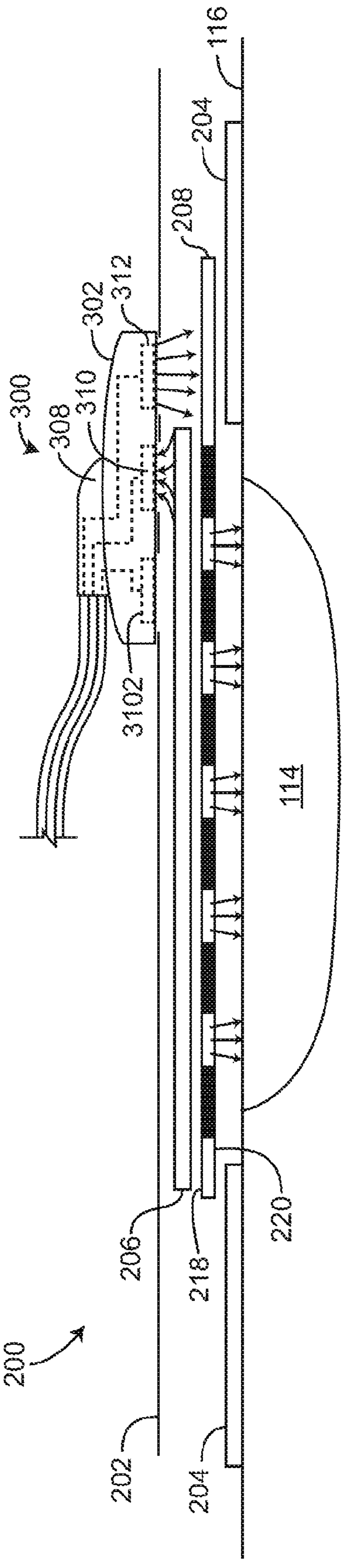
FIG. 31 is a side view of a lightguide dressing including a camera for viewing an interior of the lightguide dressing, according to some embodiments.

Referring to FIG. 31, the lightguide dressing 200 is shown to include the coupler assembly 300 for use with three devices, according to some embodiments. The coupler assembly 300 includes the first inlet/outlet 312 for providing light for phototherapy to the lightguide 208, the first inlet/outlet 310 for drawing a negative pressure at the dressing 200, and a camera 3102 for viewing an interior of the lightguide dressing 200. As shown in FIG. 31, the camera 3102 is positioned in place of the third inlet/outlet 313. In some embodiments, the camera 3102 is provided in addition to the third inlet/outlet 313 for providing instillation fluid to the interior or inner volume of the lightguide dressing 200. In some embodiments, the camera 3102 is communicably coupled with the controller 118 of the therapy device 102 to provide image data to the controller 118. In some embodiments, the camera 3102 is positioned at the coupler assembly 300. In some embodiments, the camera 3102 is positioned within the lightguide dressing 200.

In some embodiments, one or more of the layers of the lightguide dressing 200 that are between the wound 114 and the camera 3102 are transparent or translucent so that the camera 3102 can obtain image data of the wound 114. In some embodiments, the camera 3102 is a fiber optic camera. In some embodiments, one or more of the manifold layer 206, the lightguide 208, etc., are manufactured from a transparent tegaderm material that allows the camera 3102 to view the wound 114. In some embodiments, the camera 3102 is positioned below the lightguide 208 or within an opening of the lightguide 208 so that the camera 3102 has a direct line of sight to the wound 114. In some embodiments, image data obtained by the camera 3102 is provided to the controller 118 for display on a screen so that a user can view the interior of the lightguide dressing 200 without disassembly of the lightguide dressing 200. Advantageously, providing the camera 3102 facilitates real time wound monitoring capabilities so that the lightguide dressing 200 can be worn for a longer amount of time without requiring removal of the lightguide dressing 200 and potential disruption of the wound 114.

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A wound dressing for use with a negative pressure wound therapy (NPWT) device, the wound dressing comprising:

a manifold layer configured to extend over a wound for NPWT;

a lightguide configured to be positioned below the manifold layer and above the wound, the lightguide configured to receive light at a first portion, transfer the light through the lightguide, and emit the light towards the wound at a second portion;

a drape layer covering the manifold layer and the lightguide, the drape layer configured to sealingly couple with skin surrounding the wound and defining a sealed inner volume of the wound dressing;

wherein the drape layer comprises a first opening and a second opening; and a coupler assembly comprising:

a coupler configured to couple with the first opening and the second opening of the drape layer, a first tubular member configured to fluidly couple with the first opening of the wound dressing through the coupler for drawing the negative pressure at the wound; and a second tubular member operably coupled with the second opening through the coupler for delivering light to the wound for phototherapy.

2. The wound dressing of claim 1, wherein the lightguide comprises a plurality of openings extending through the lightguide, the plurality of openings configured to define a path for fluid to transfer from the wound to the manifold layer through the lightguide when the negative pressure is drawn at the wound.

3. The wound dressing of claim 2, wherein the plurality of openings are arranged in an array.

4. The wound dressing of claim 3, wherein at least one of a size or a shape of the openings varies along at least one dimension of the array.

5. The wound dressing of claim 3, wherein a size and a shape of the openings is uniform along at least one dimension of the array.

6. The wound dressing of claim 1, wherein the coupler assembly comprises a light source positioned within the coupler configured to emit light through the second opening to the lightguide, and wherein the second tubular member is a wire configured to provide electrical energy to the light source.

7. The wound dressing of claim 1, wherein the second tubular member is a fiber optic cable configured to receive light from an external light source and provide the light through the second tubular member to the lightguide through the second opening.

8. The wound dressing of claim 1, wherein the coupler assembly further comprises a third tubular member configured to fluidly couple with a third opening of the drape layer, wherein the third tubular member is configured to provide an instillation fluid to the sealed inner volume of the wound dressing through the third opening of the drape.

9. The wound dressing of claim 8, wherein the instillation fluid includes a photosensitizing agent, wherein the photosensitizing agent is configured to increase an absorption of the light into tissue of the wound.

10. The wound dressing of claim 9, wherein the photosensitizing agent is Methylene blue or O-toluidine blue.

11. The wound dressing of claim 1, wherein an interior surface of the drape layer comprises a reflective material, wherein the reflective material is configured to reflect light towards the wound to improve an efficacy of the phototherapy.

12. A negative pressure wound therapy (NPWT) and phototherapy system, the system comprising:

a wound dressing configured to cover a wound;

a therapy device configured to draw a negative pressure at the wound for NPWT;

a light source configured to provide light to the wound within the wound dressing for photo therapy; and a coupler assembly configured to be coupled to the wound dressing, the coupler assembly comprising:

a coupler configured to couple with a first opening and a second opening of the wound dressing, a first tubular member configured to fluidly couple the therapy device with the first opening of the wound dressing through the coupler for drawing the negative pressure at the wound; and a second tubular member operably coupled with the second opening of the wound dressing through the coupler for delivering light from the light source to the wound dressing for phototherapy;

wherein the system is configured to provide both NPWT and phototherapy to the wound consecutively or at least partially concurrently, wherein providing NPWT changes a surface topology of the wound prior to or at least partially concurrently with providing phototherapy.

13. The system of claim 12, wherein the wound dressing comprises:

a manifold layer over the wound for NPWT;

a lightguide configured to be positioned below the manifold layer and above the wound, the lightguide configured to receive light at a first portion, transfer the light through the lightguide, and emit the light towards the wound at a second portion for the phototherapy of the wound; and a drape layer covering the manifold layer and the lightguide, the drape layer configured to sealingly couple with skin surrounding the wound and defining a sealed inner volume of the wound dressing;

wherein the drape layer comprises the first opening for drawing a negative pressure at the sealed inner volume of the wound dressing, and the second opening for providing light to the first portion of the lightguide for the phototherapy of the wound.

14. The system of claim 12, wherein the light source is positioned external to the wound dressing.

15. The system of claim 12, wherein the light source is positioned within the therapy device.

16. The system of claim 12, wherein the light provided by the light source is at least one of visible light, UV light, blue light, infrared light, near infrared light, or red light.

17. The system of claim 12, wherein the light provided by the light source is visible light, and a plurality of microfilm layers are positioned between the light source and the wound, wherein the plurality of microfilm layers are configured to filter the light so that light having a different wavelength is provided to the wound for the phototherapy.

18. The system of claim 12, wherein the light source is configured to operate to provide light having a first wavelength over a first time period and light having a second wavelength over a second time period to provide different types of phototherapy.

* * * * *